United States Patent
Tesar et al.

(10) Patent No.: US 10,653,691 B2
(45) Date of Patent: *May 19, 2020

(54) METHOD OF PROMOTING REMYELINATION

(71) Applicant: Case Western Reserve University, Cleveland, OH (US)

(72) Inventors: Paul J. Tesar, Wickliffe, OH (US); Fadi J. Najm, Cleveland, OH (US); Robert H. Miller, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,576

(22) Filed: Dec. 21, 2018

(65) Prior Publication Data

US 2019/0209554 A1 Jul. 11, 2019

Related U.S. Application Data

(63) Continuation of application No. 14/723,008, filed on May 27, 2015, now Pat. No. 10,195,194, which is a continuation-in-part of application No. PCT/US2014/057471, filed on Sep. 25, 2014.

(60) Provisional application No. 61/882,419, filed on Sep. 25, 2013, provisional application No. 61/882,861, filed on Sep. 26, 2013, provisional application No. 62/003,109, filed on May 27, 2014.

(51) Int. Cl.
| | |
|---|---|
| *A61K 31/496* | (2006.01) |
| *A61K 31/57* | (2006.01) |
| *A61K 31/4174* | (2006.01) |
| *A61K 31/573* | (2006.01) |

(52) U.S. Cl.
CPC ........ *A61K 31/496* (2013.01); *A61K 31/4174* (2013.01); *A61K 31/57* (2013.01); *A61K 31/573* (2013.01)

(58) Field of Classification Search
CPC ................ A61K 31/496; A61K 31/573; A61K 31/4174; A61K 31/57
See application file for complete search history.

(56) References Cited

U.S. PATENT DOCUMENTS

| | | |
|---|---|---|
| 10,195,194 B2 | 2/2019 | Tesar et al. |
| 2010/0298394 A1 | 11/2010 | Steiner et al. |
| 2012/0231052 A1 | 9/2012 | Sitruk-Ware et al. |

OTHER PUBLICATIONS

Kipp et al., Multiple sclerosis: neuroprotective alliance of estrogen-progesterone and gender. Front Neuroendocrinol. Jan. 2012;33(1):1-16.

Najm et al., Drug-based modulation of endogenous stem cells promotes functional remyelination in vivo. Nature. Jun. 11, 2015;522(7555):216-20.

(Continued)

*Primary Examiner* — Angela C Brown-Pettigrew
(74) *Attorney, Agent, or Firm* — McCarter & English, LLP; Steven G. Davis

(57) ABSTRACT

A method of promoting remyelination in a subject in need thereof includes administering to the subject a therapeutically effective amount of at least one (1,3) Diazole compound, wherein the therapeutically effective amount is the amount effective to induce endogenous oligodendrocyte precursor cell (OPC) differentiation in the subject's central nervous system.

9 Claims, 28 Drawing Sheets

(56) References Cited

OTHER PUBLICATIONS

Fitzner et al., Chronic progressive multiple sclerosis—pathogenesis of neurodegeneration and therapeutic strategies. Curr Neuropharmacol. Sep. 2010;8(3):305-15.
Rodgers et al., Strategies for protecting oligodendrocytes and enhancing remyelination in multiple sclerosis. Discov Med. Aug. 2013;16(86):53-63.
PubChem CID: 16759250. DBPWSSGDRRHUNT-NWQZBTRTSA-N. 14 pages. Jul. 21, 2018.
Swenson et al., Demyelinating diseases of the nervous system. Disorders of the Nervous System—Reeves & Swenson. Chapter 23, 6 pages. Retrieved online at: https://www.dartmouth.edu/~dons/part_3/chapter_23.html. (2008).

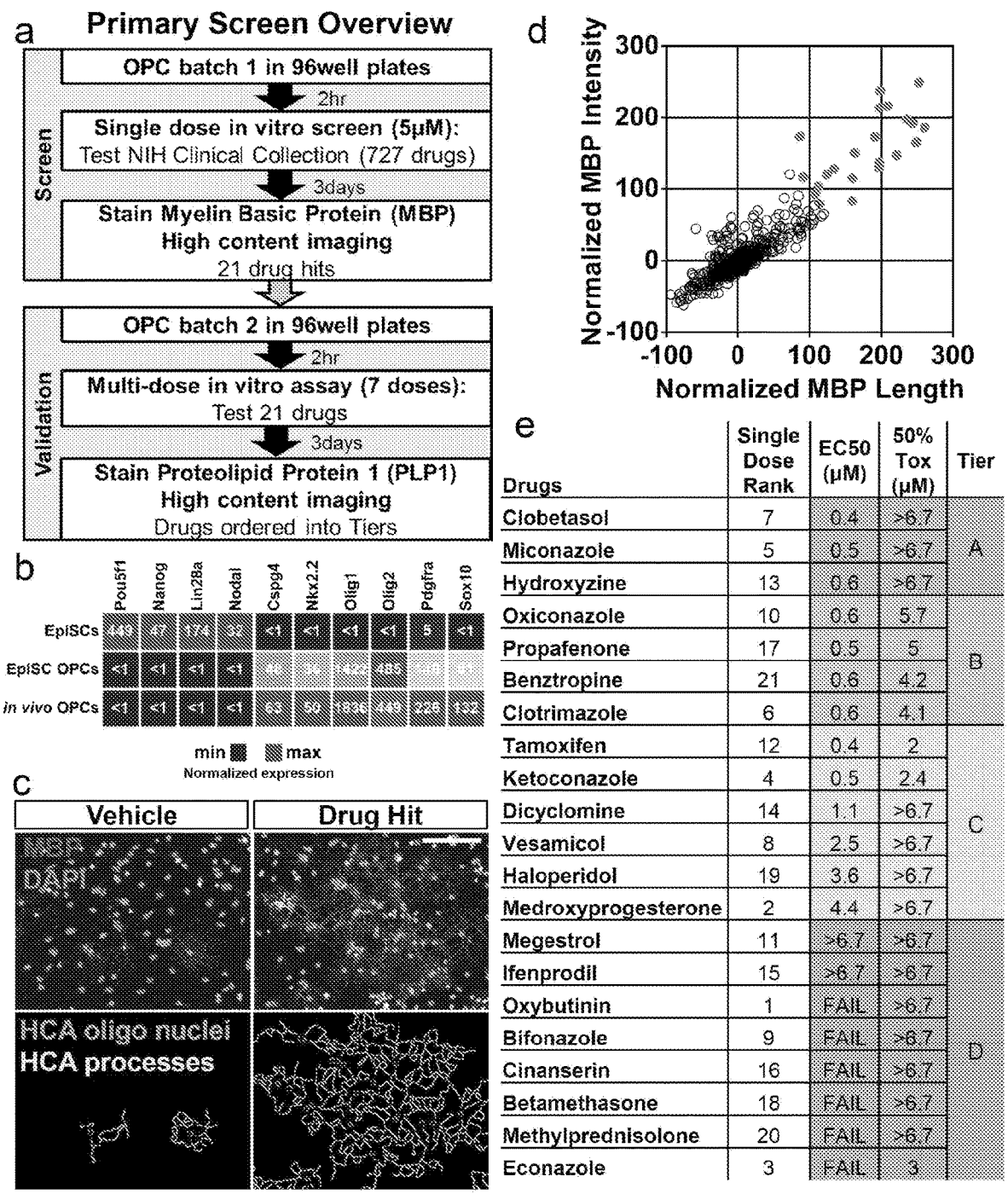
Figs. 1A-E

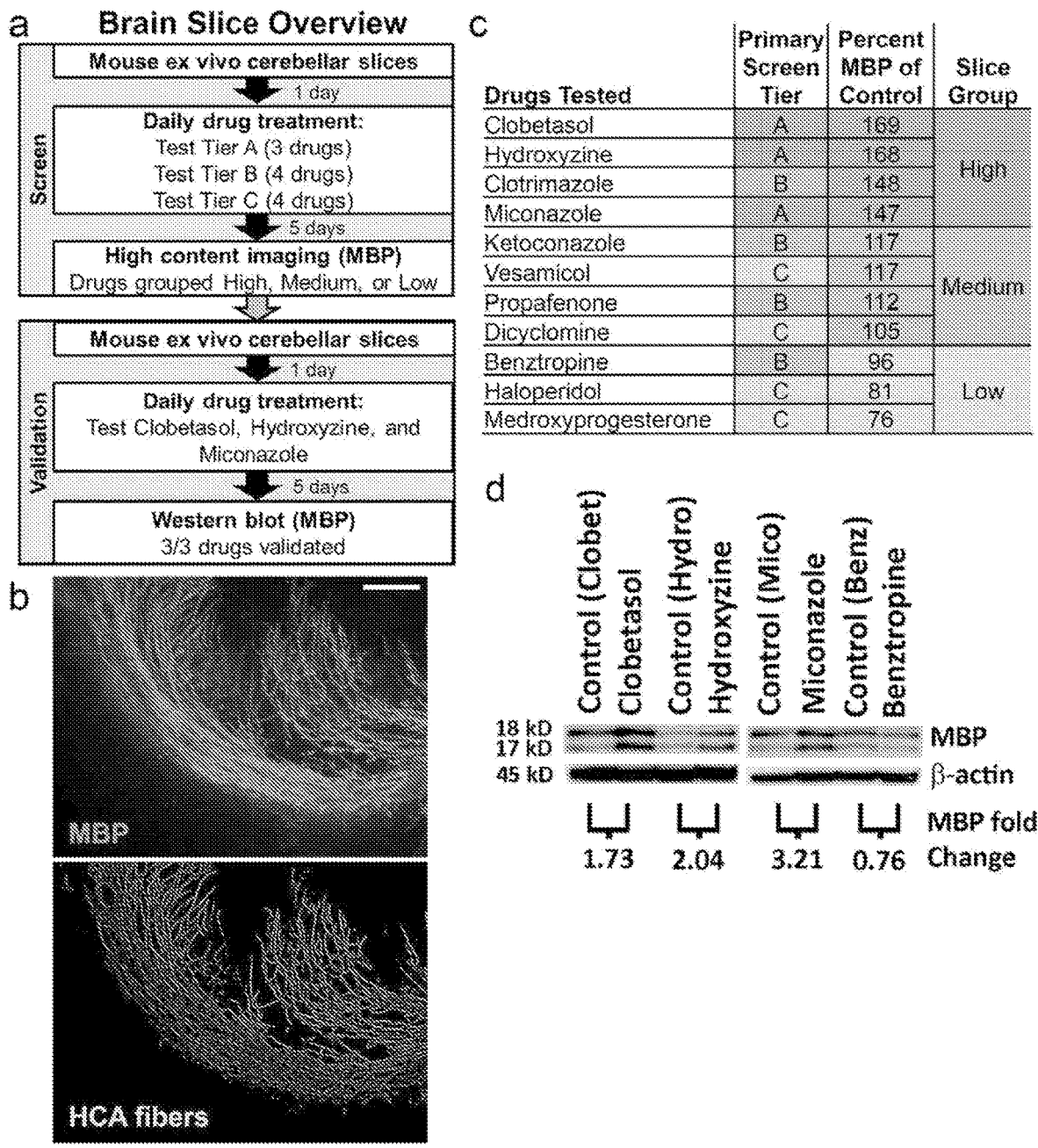
Figs. 2A-D

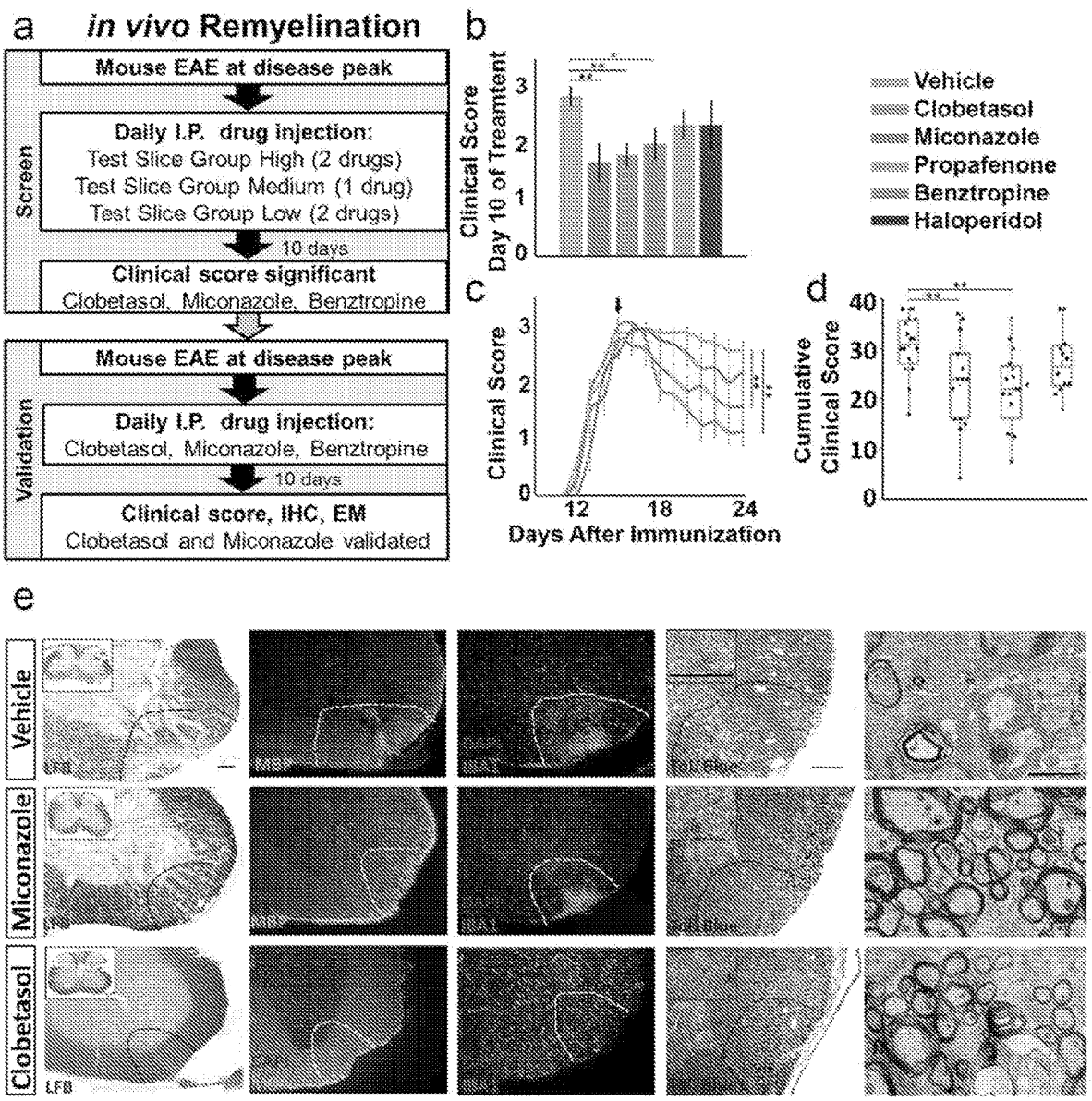
Figs. 3A-E

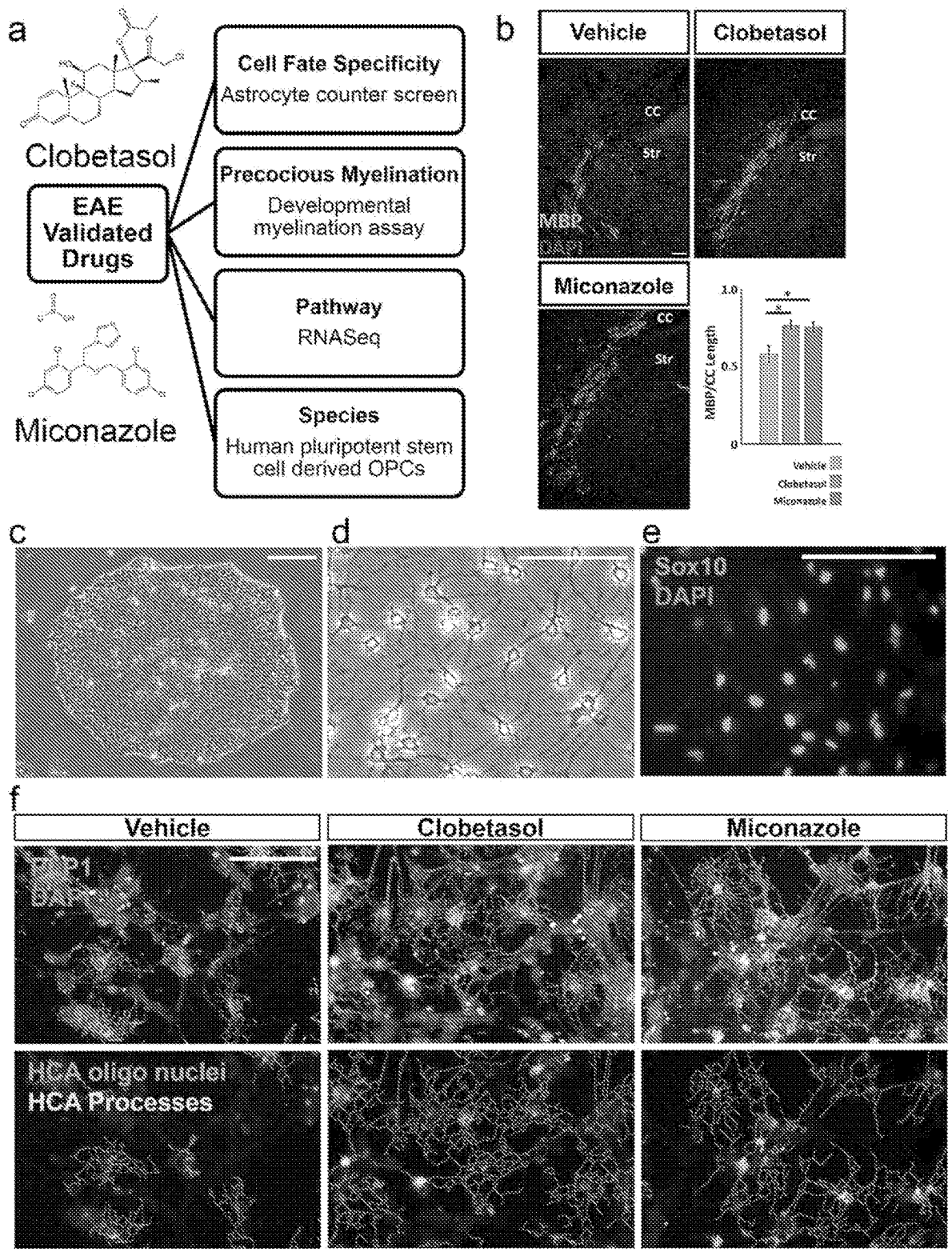
Figs. 4A-F

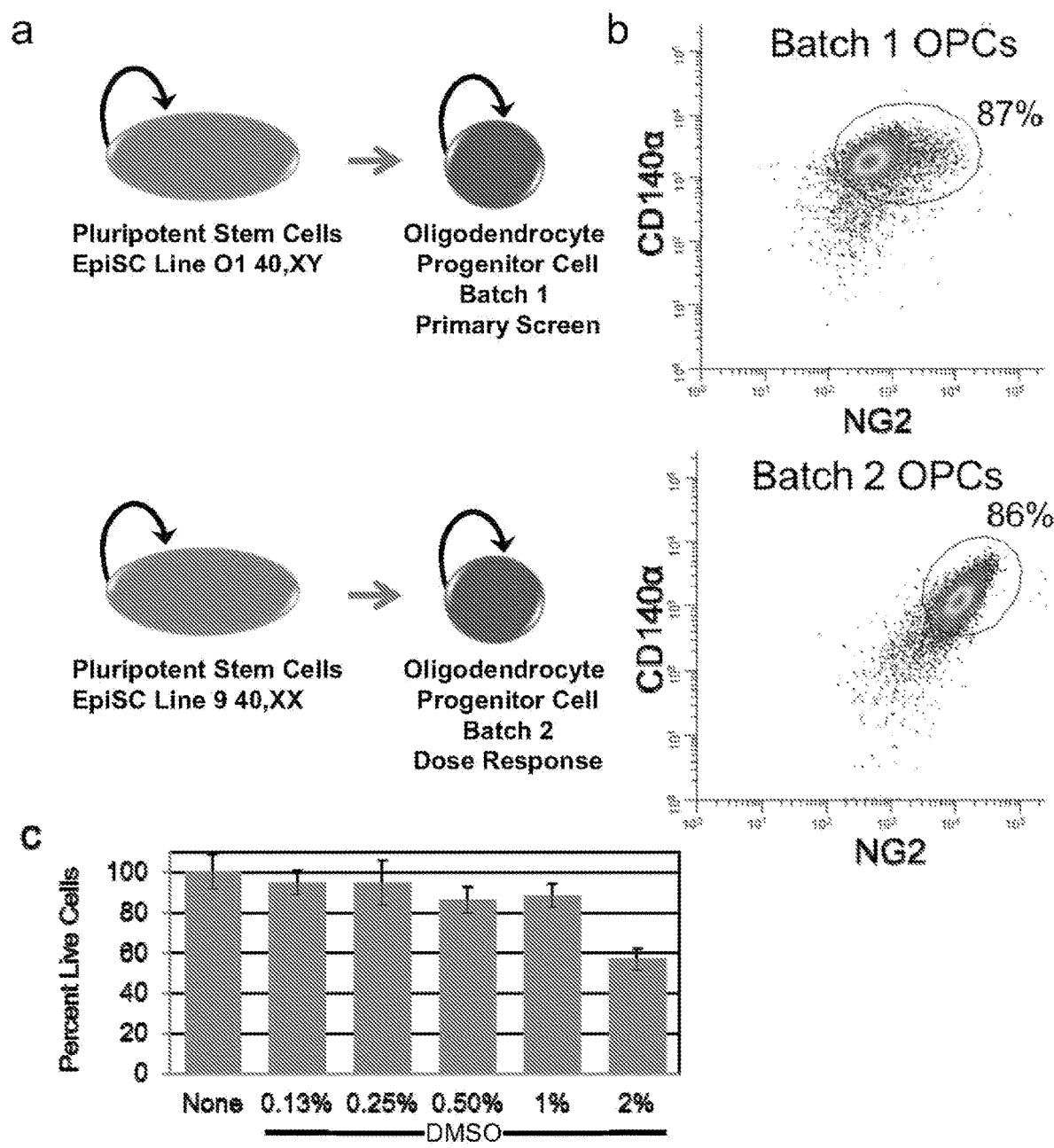
Figs. 5A-C

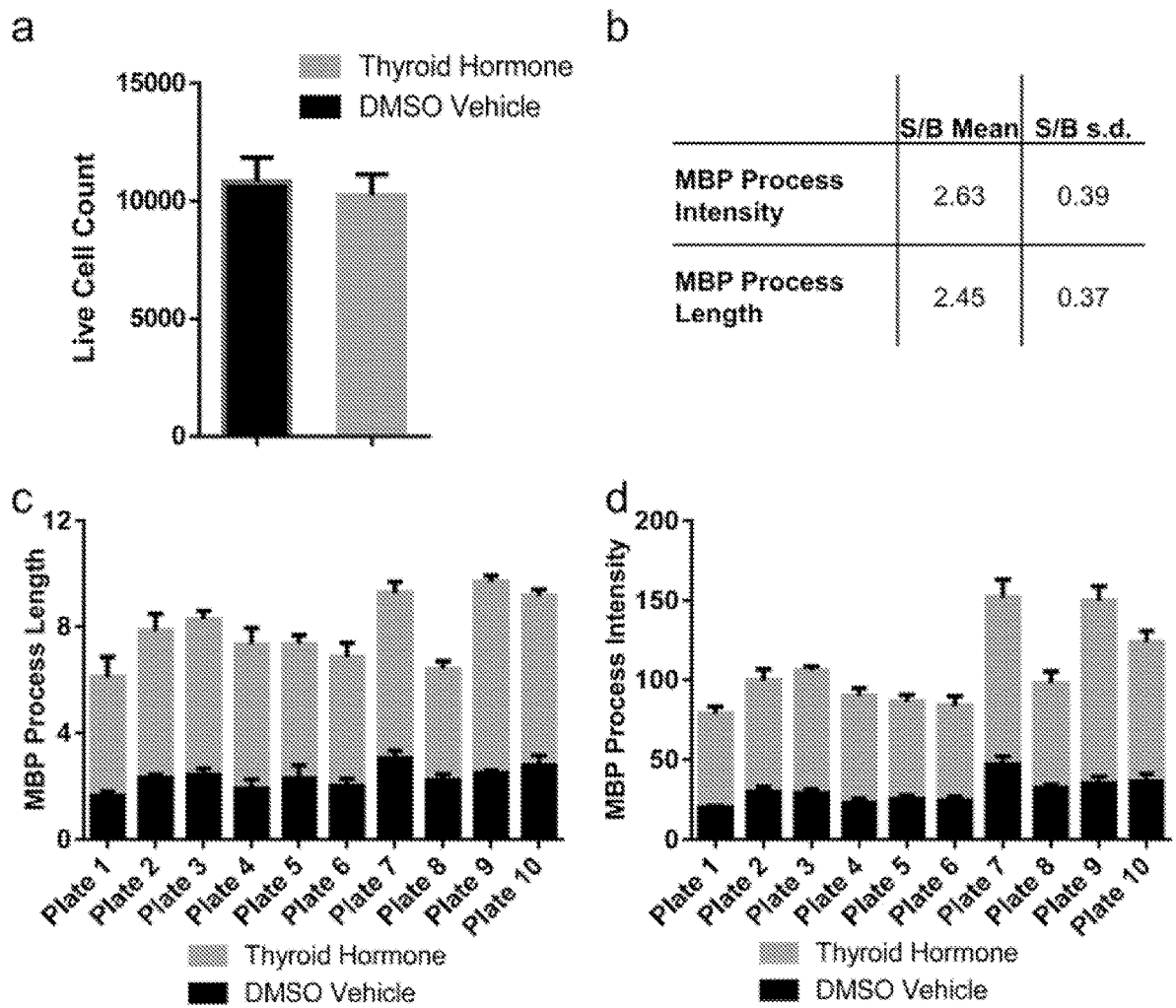
Figs. 6A-D a
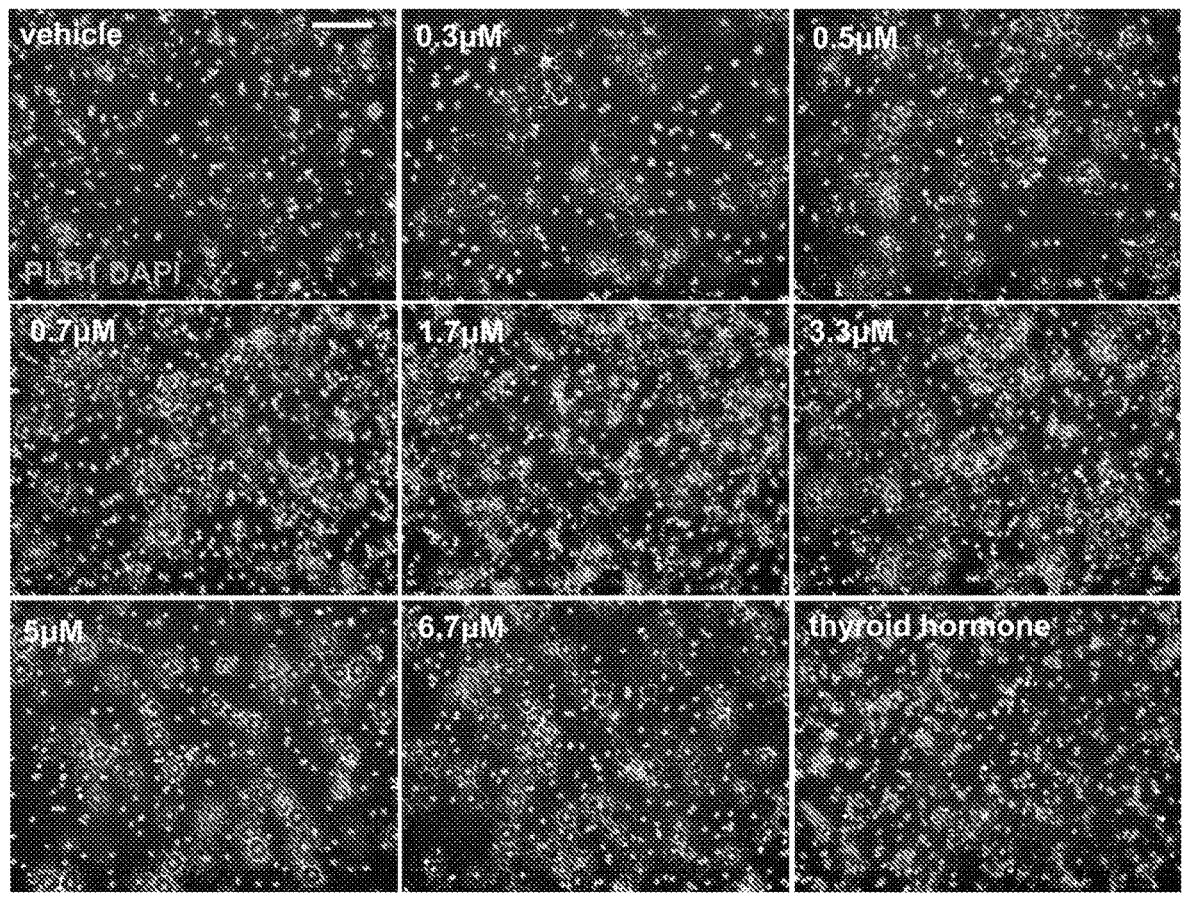
b
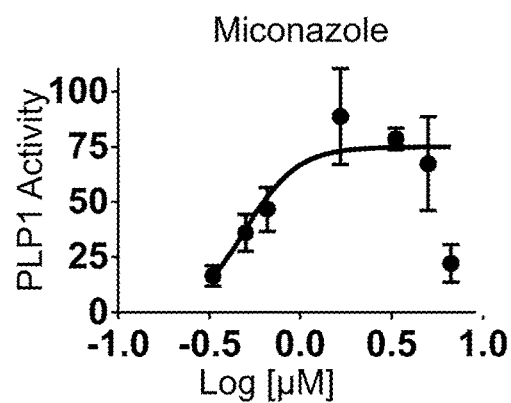
Figs. 7A-B a
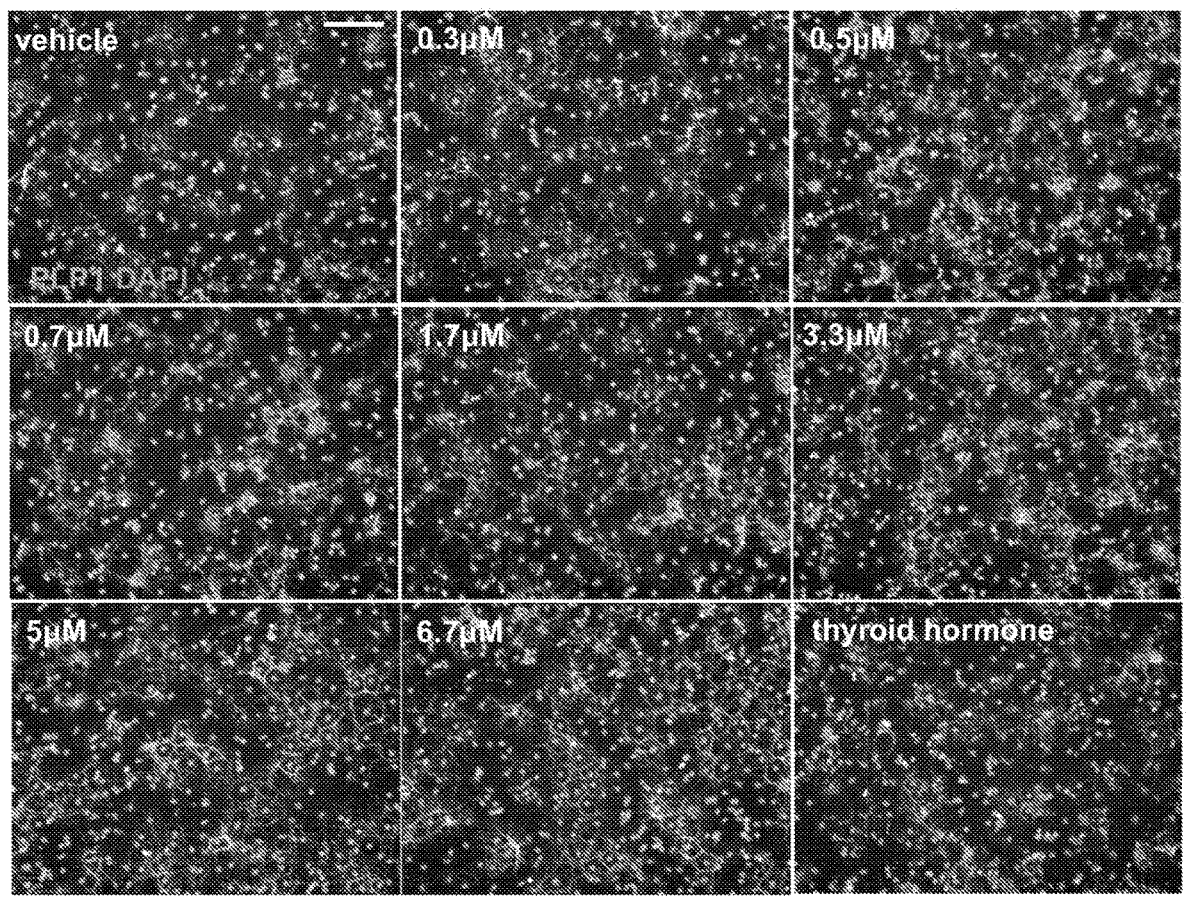
b
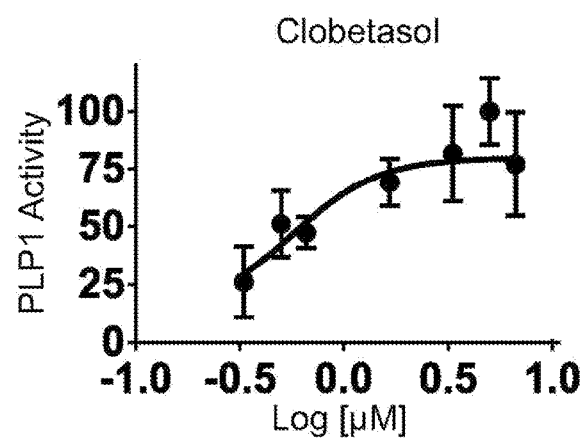
Figs. 8A-B

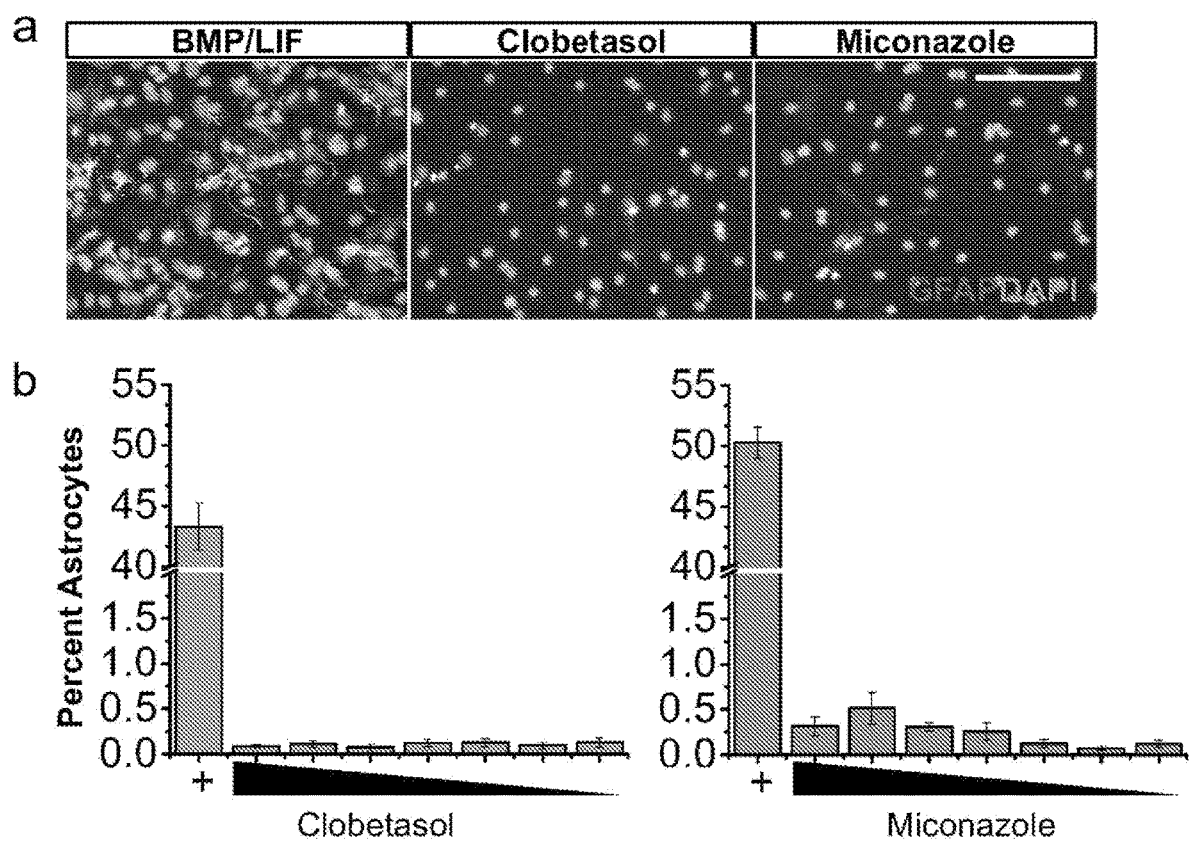
Figs. 11A-B

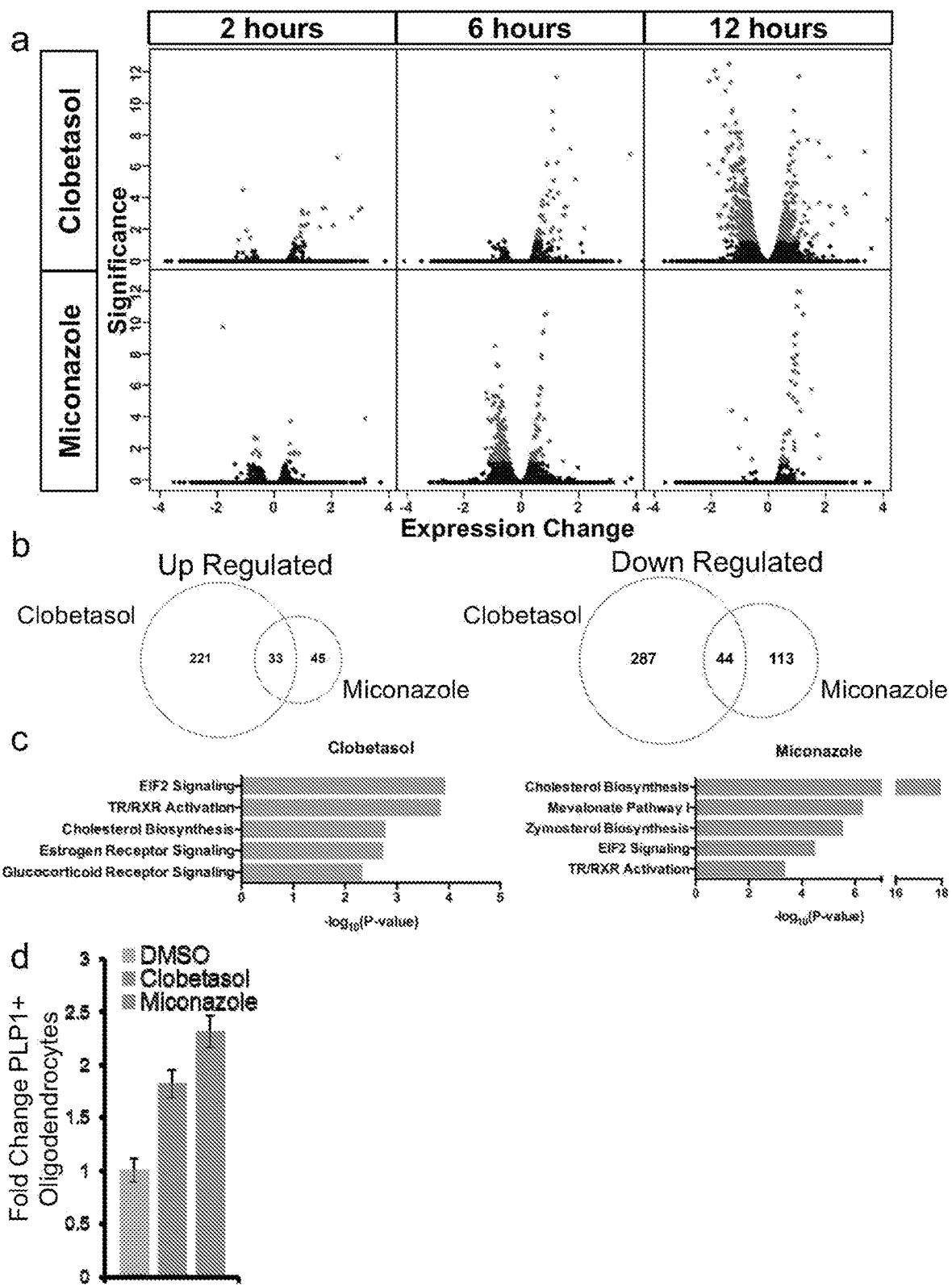
Figs. 12A-D

EAE Hit

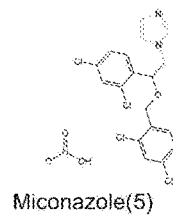

Miconazole(5)

Free (1,3) Diazoles

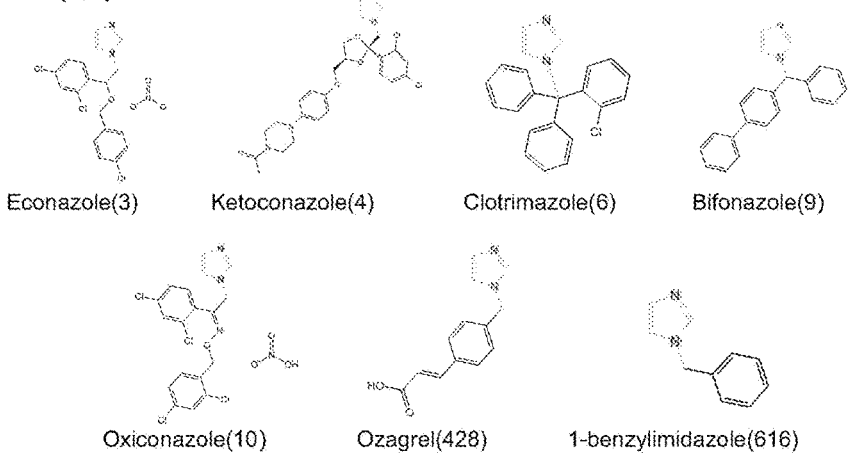

Econazole(3)  Ketoconazole(4)  Clotrimazole(6)  Bifonazole(9)

Oxiconazole(10)  Ozagrel(428)  1-benzylimidazole(616)

Bound (1,3) Diazoles

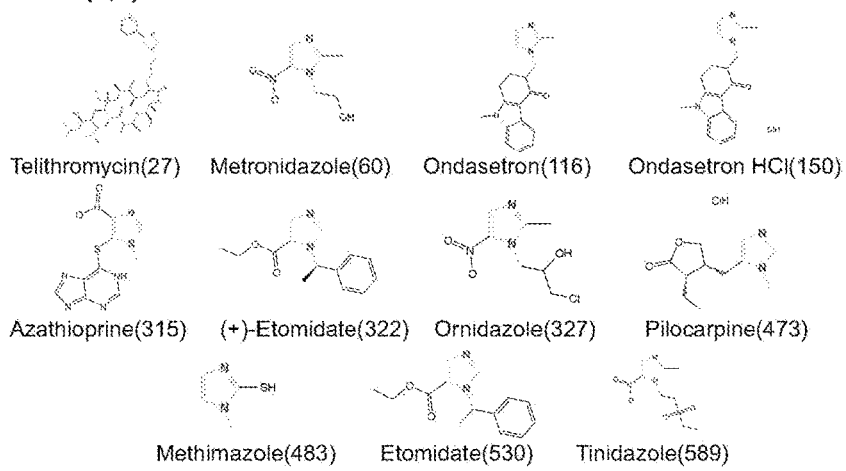

Telithromycin(27)  Metronidazole(60)  Ondasetron(116)  Ondasetron HCl(150)

Azathioprine(315)  (+)-Etomidate(322)  Ornidazole(327)  Pilocarpine(473)

Methimazole(483)  Etomidate(530)  Tinidazole(589)

(1,2,4) Triazoles

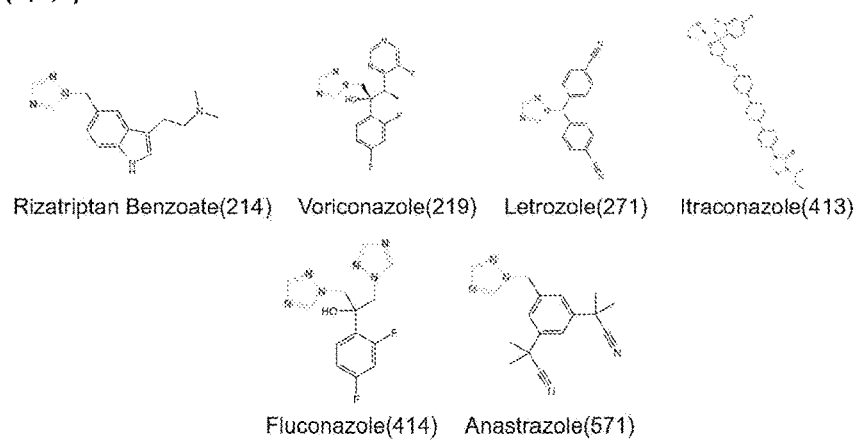

Rizatriptan Benzoate(214)  Voriconazole(219)  Letrozole(271)  Itraconazole(413)

Fluconazole(414)  Anastrazole(571)

Fig. 13

EAE Hit

Clobetasol(7)

Steroids

Betamethasone(19)　Methylprednisolone(21)　Budesonide(28)　Triamcinolone(29)

Amcinonide(35)　Fluticasone(37)　Fluorometholone(38)　Depo-medrol(41)

Beclomethasone(44)　Loteprednol(45)　Fluocinolone(47)　Dexamethasone(49)

Hydrocortisone(50)　Halometasone(52)　Fluocinonide(57)　Prednisolone(67)

Beclomethasone(73)　Prednisolone(83)　Desoximetasone(100)

Dehydrocholic Acid(188)　Mestanolone(198)　Exemestane(212)

Flunisolide(259)　Prednisone(528)

Fig. 14

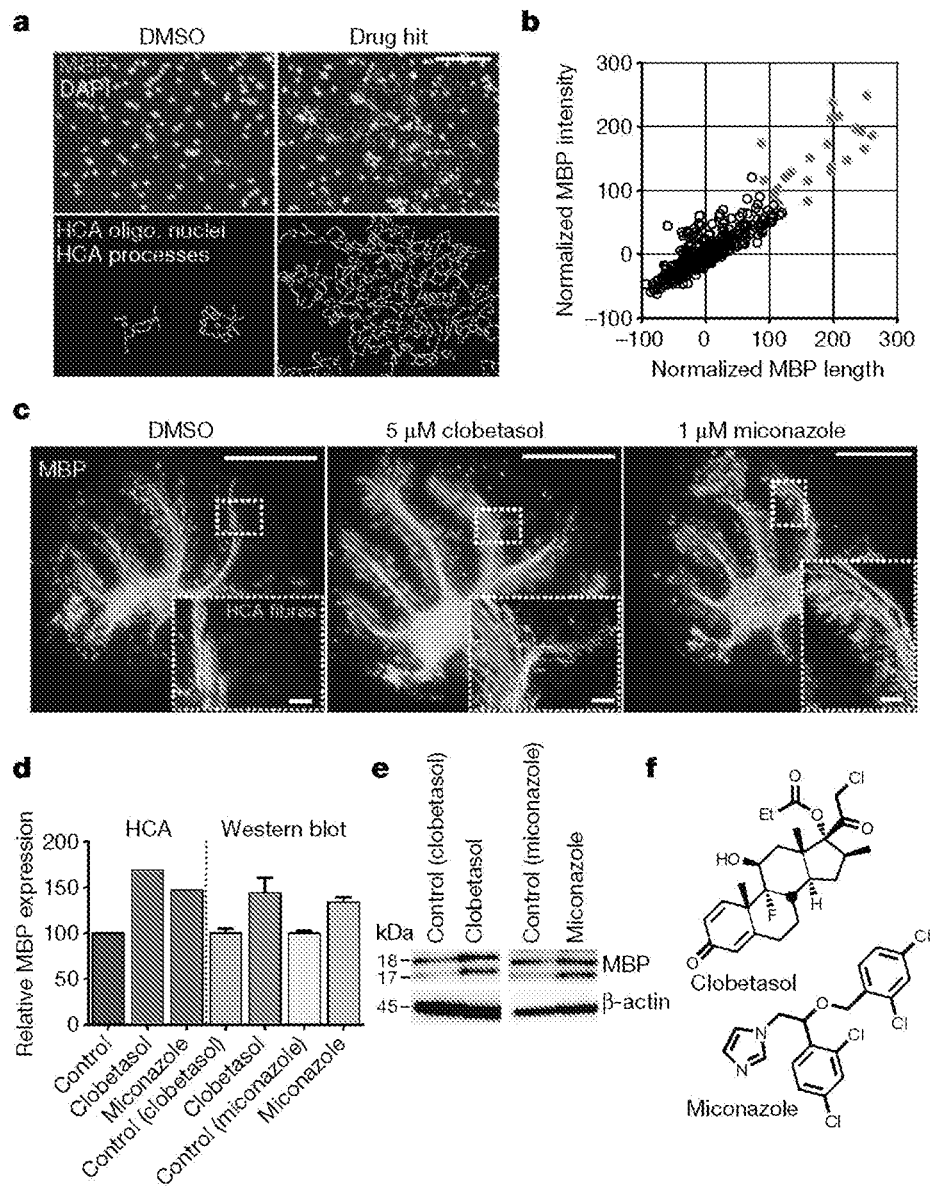
Figs. 15A-F

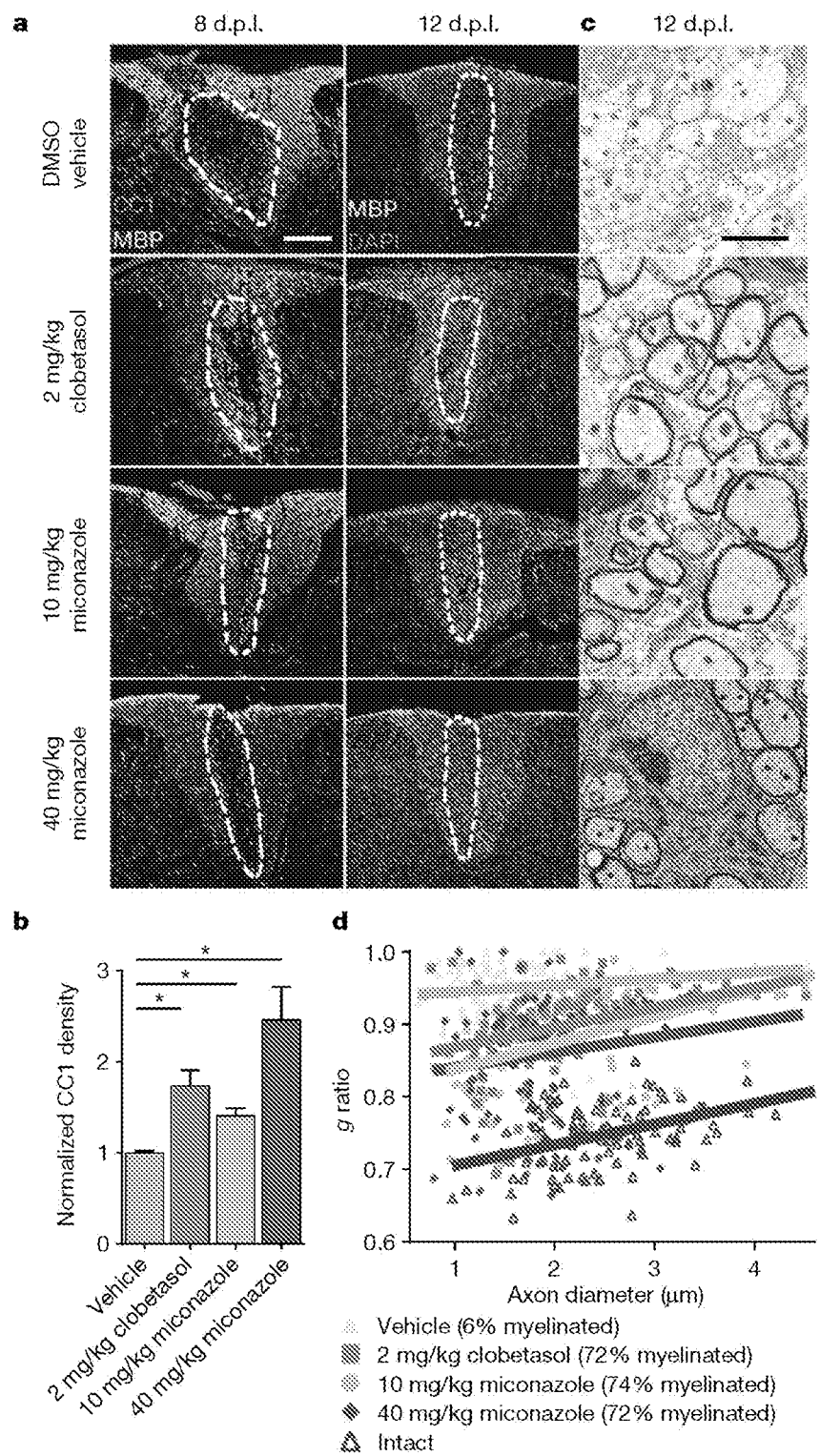
Figs. 16A-D

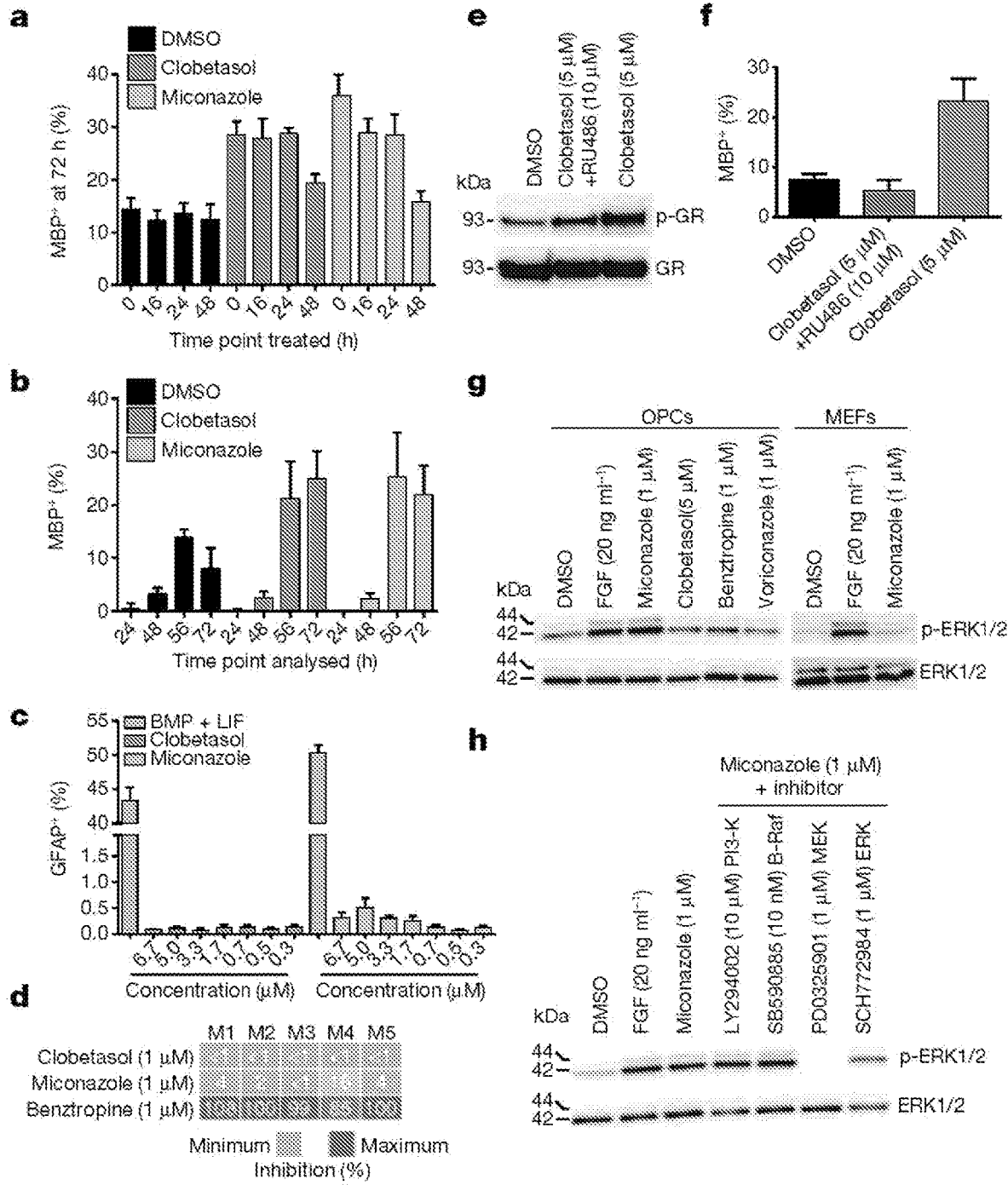
Figs. 17A-H

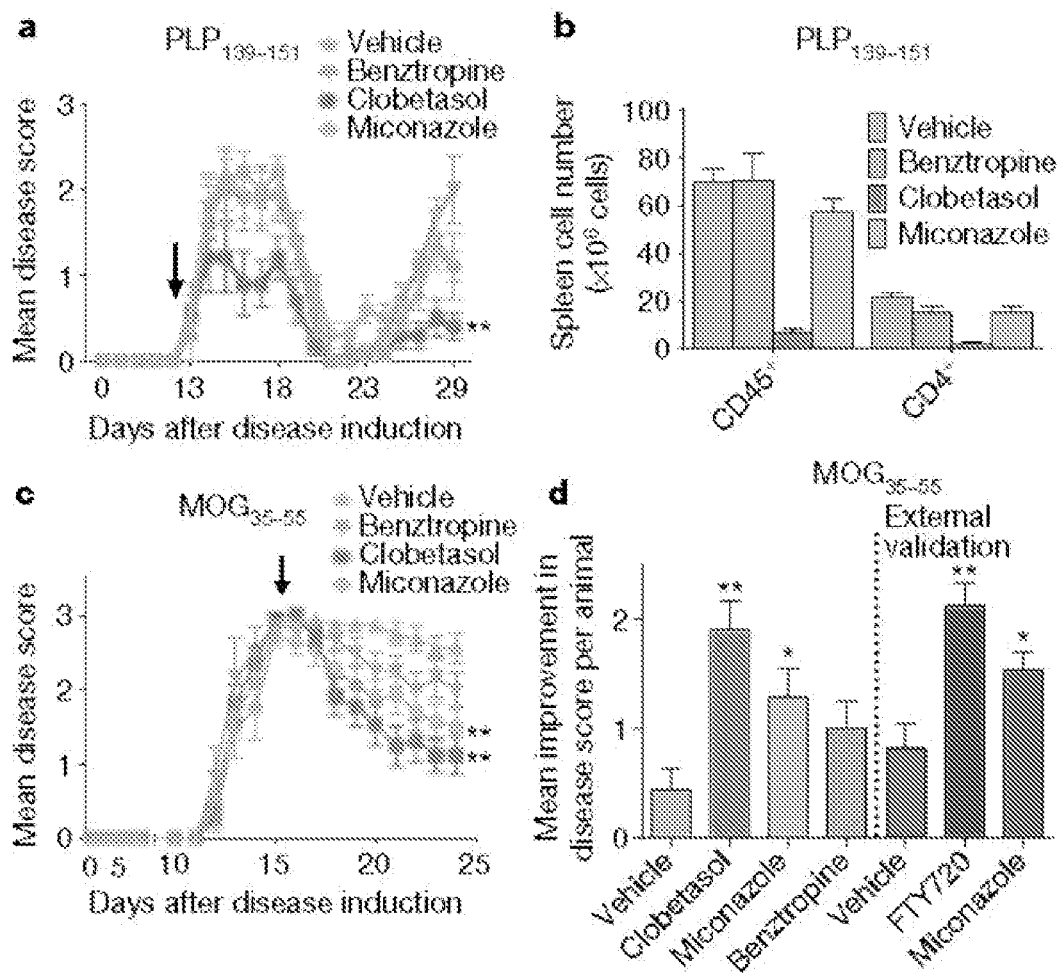
Figs. 18A-D

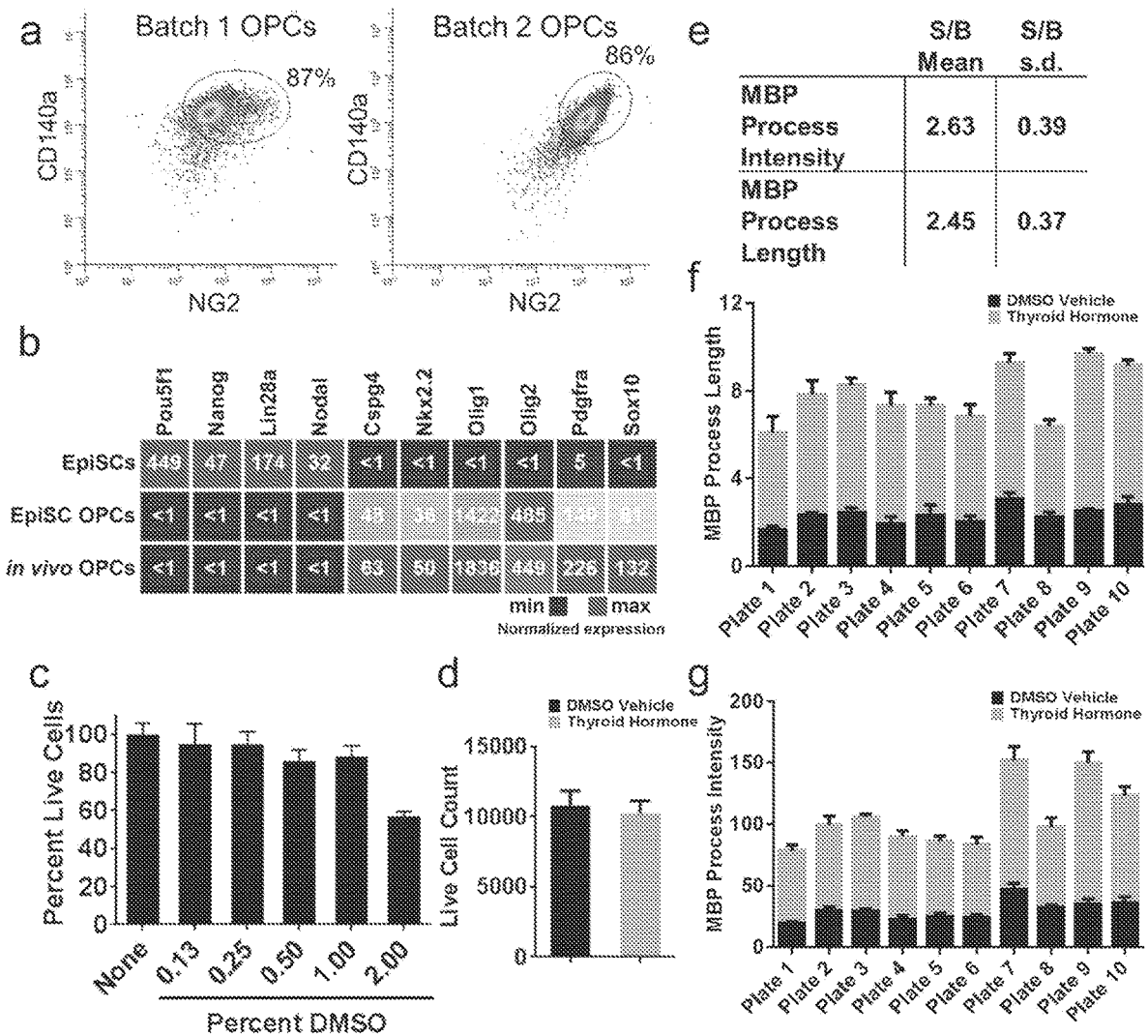
Figs. 19A-G

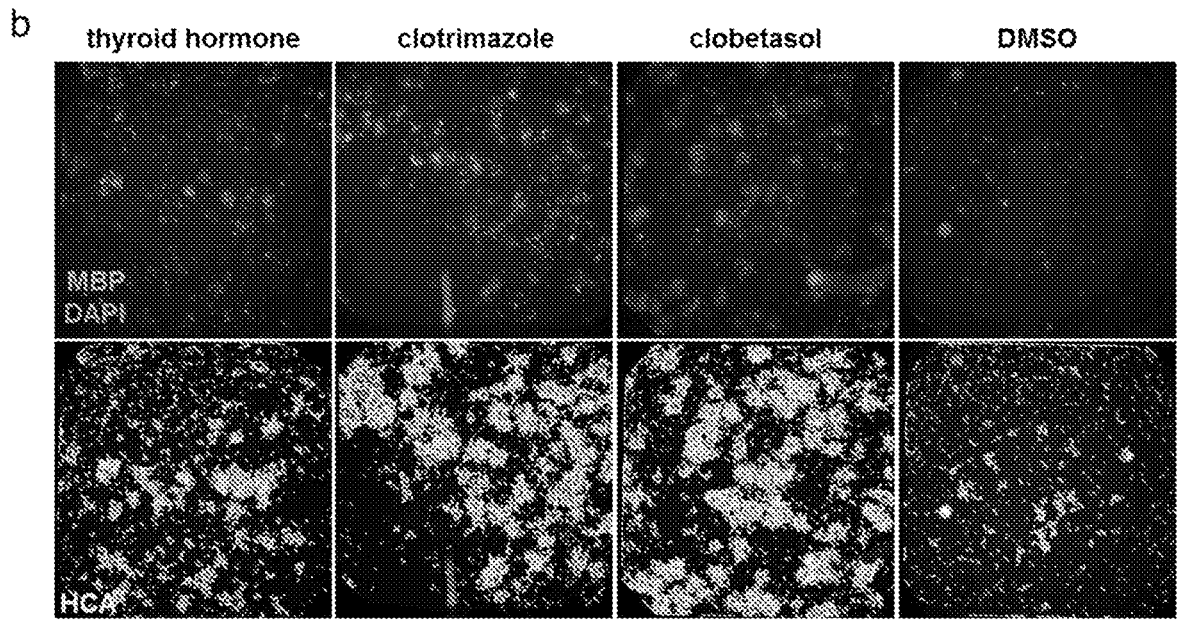
Figs. 20A-B a 

| (1,3) Diazoles, mono-substituted at the 1-position | Primary Screen Rank |
|---|---|
| econazole | 3 |
| ketoconazole | 4 |
| miconazole | 5 |
| clotrimazole | 6 |
| bifonazole | 9 |
| oxiconazole | 10 |
| ozagrel | 428 |
| 1-benzylimidazole | 616 | b 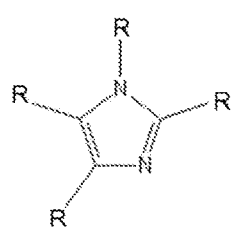

| (1,3) Diazoles, poly-substituted | Primary Screen Rank |
|---|---|
| telithromycin | 27 |
| metronidazole | 60 |
| ondansetron | 116 |
| azathioprine | 315 |
| (+)-etomidate | 322 |
| ornidazole | 327 |
| pilocarpine | 473 |
| methimazole | 483 |
| tinidazole | 589 | c 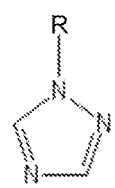

| (1,2,4) Triazoles, mono-substituted at the 1-position | Primary Screen Rank |
|---|---|
| rizatriptan | 214 |
| voriconazole | 219 |
| letrozole | 271 |
| itraconazole | 413 |
| fluconazole | 414 |
| anastrazole | 571 | d

| Steroids | Primary Screen Rank |
|---|---|
| clobetasol | 7 |
| betamethasone | 19 |
| methylprednisolone | 21 |
| budesonide | 28 |
| triamcinolone | 29 |
| amcinonide | 35 |
| fluticasone | 37 |
| fluorometholone | 38 |
| depo-medrol | 41 |
| beclomethasone | 44 |
| loteprednol | 45 |
| fluocinolone | 47 |
| dexamethasone | 49 |
| hydrocortisone | 50 |
| halometasone | 52 |
| flucinonide | 57 |
| prednisolone | 67 |
| desoximetasone | 100 |
| dehydrocholic Acid | 188 |
| mestanolone | 198 |
| exemestane | 212 |
| flunisolide | 259 |
| prednisone | 528 |

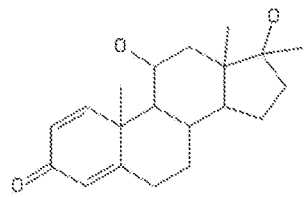

Figs. 21A-D

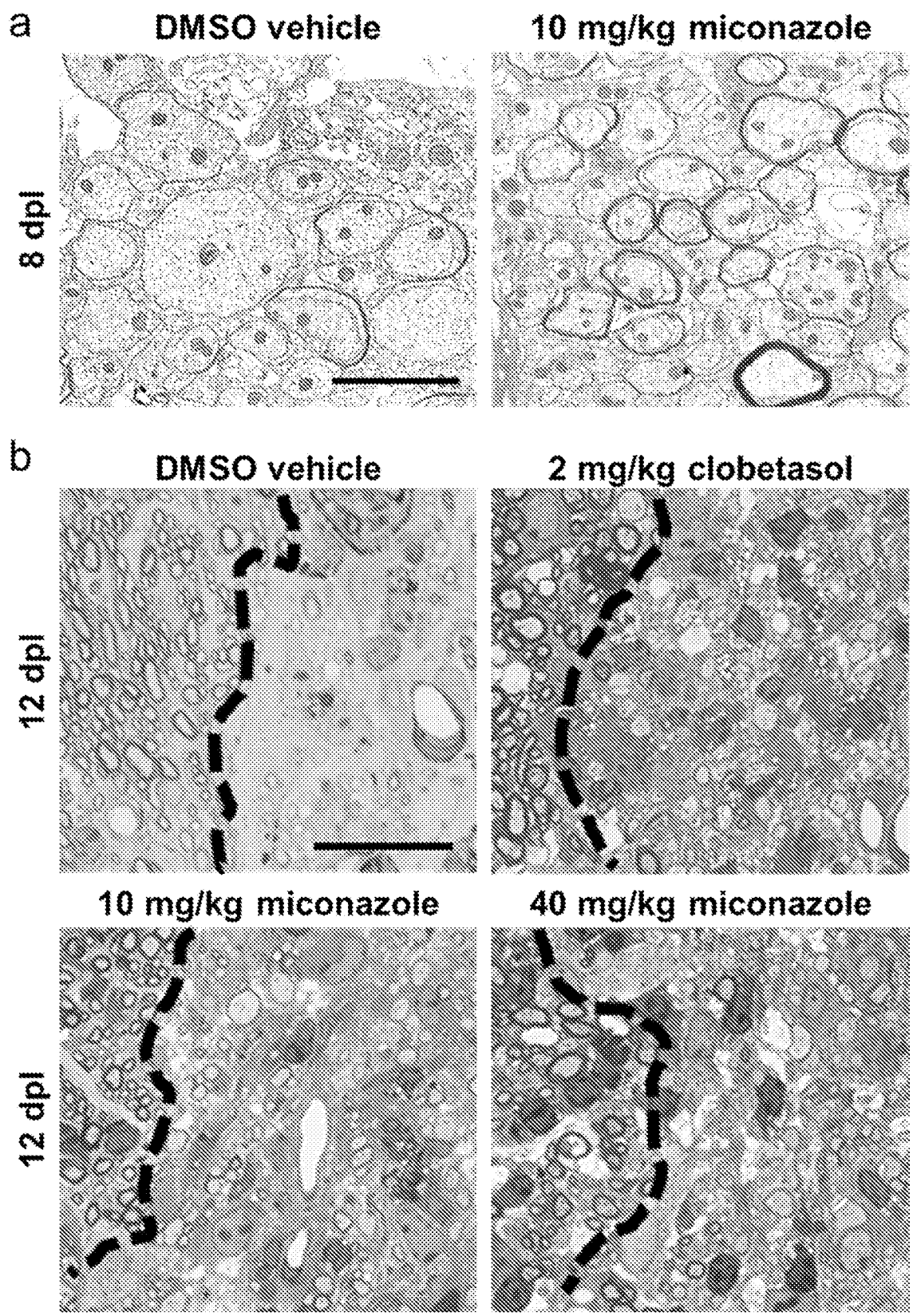
Figs. 22A-B

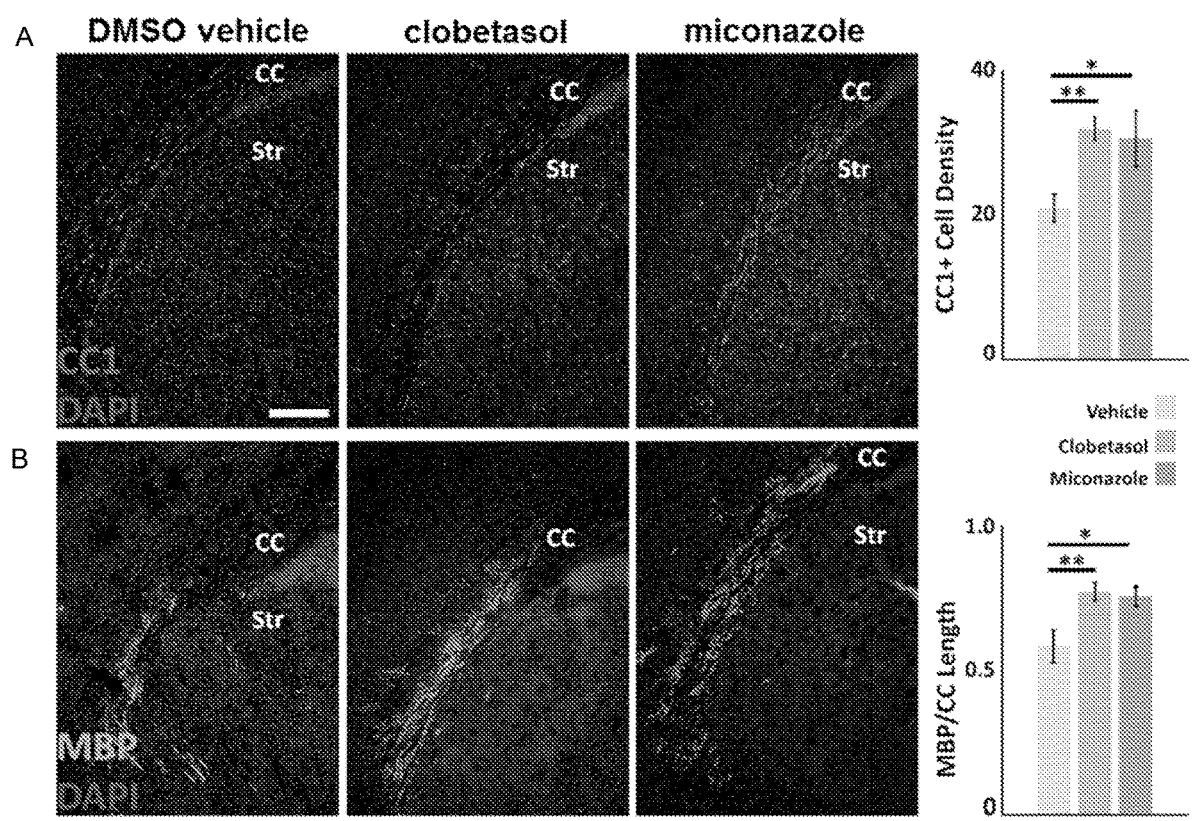
Figs. 23A-B

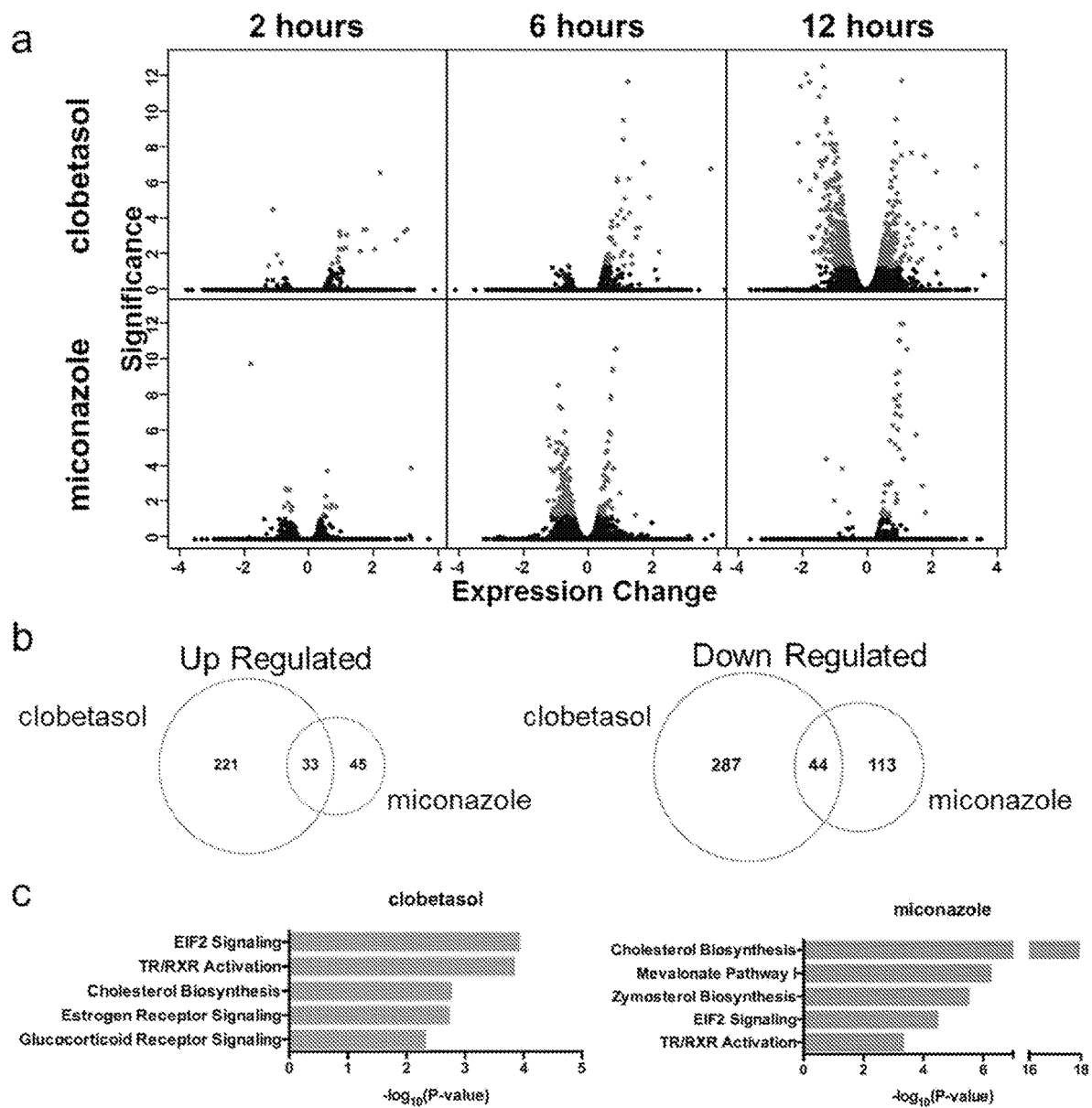
Figs. 24A-C

A
B
C
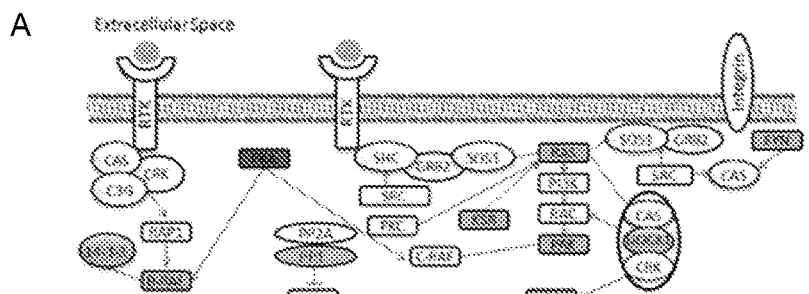
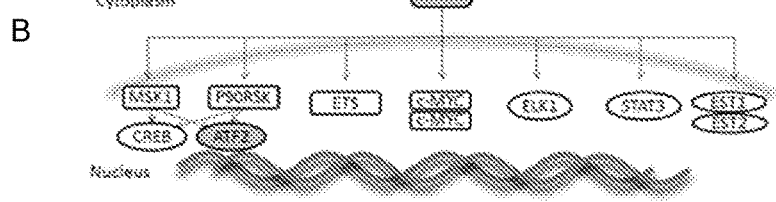
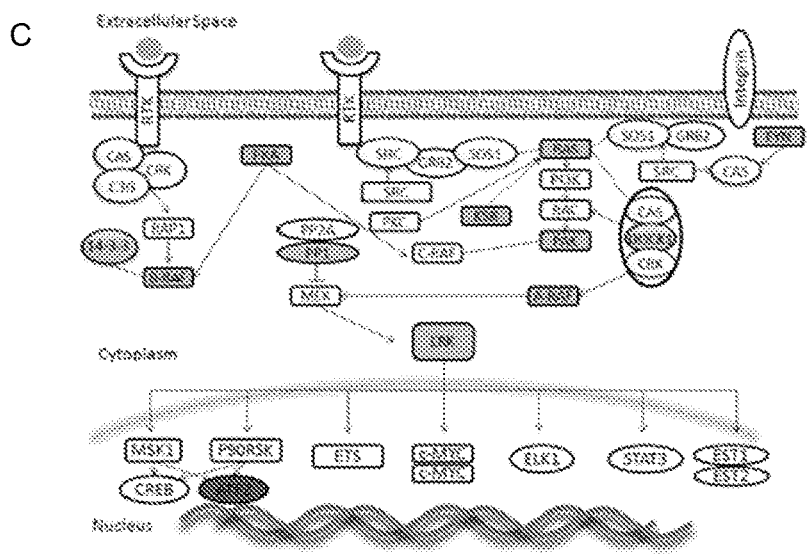
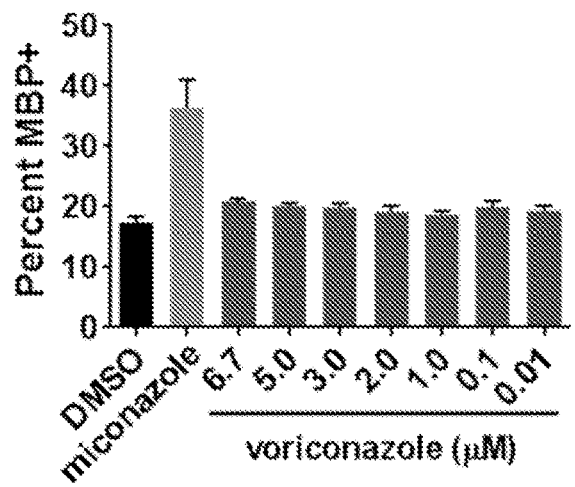
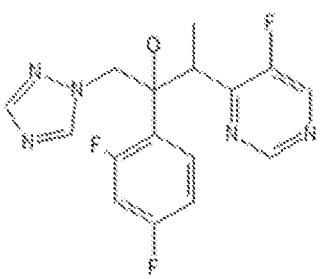
Figs. 25A-C

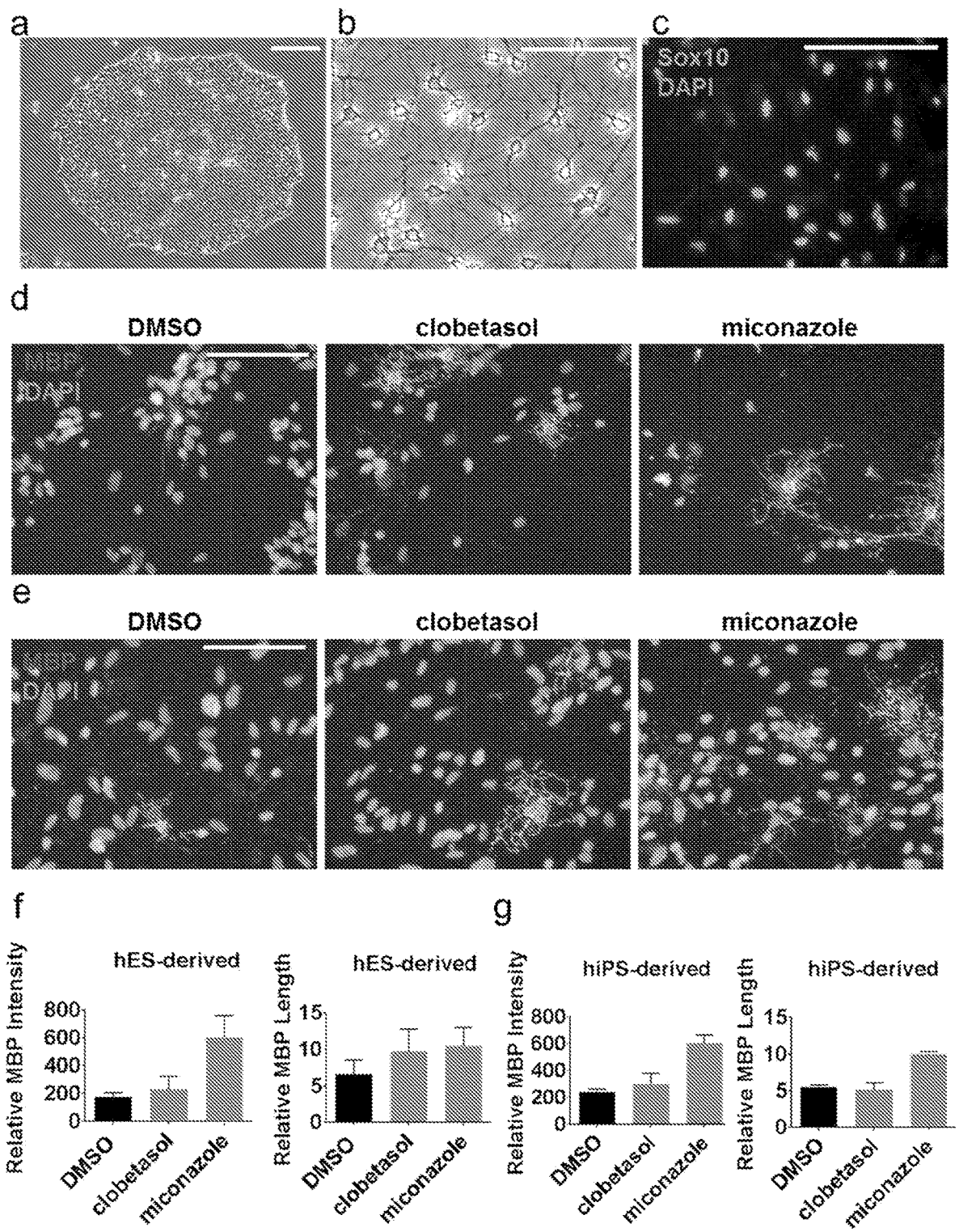
Figs. 26A-G

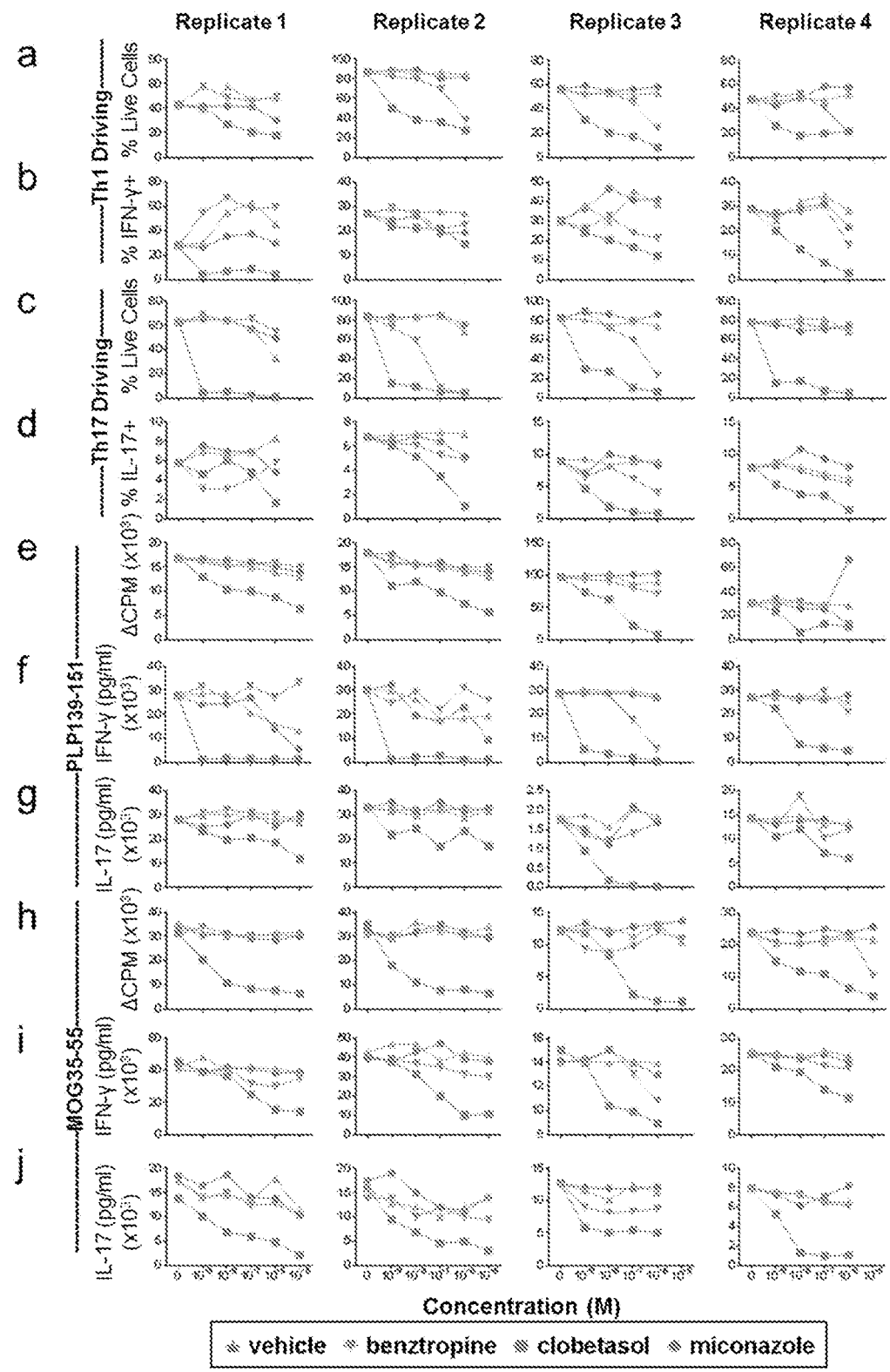
Figs. 27A-J

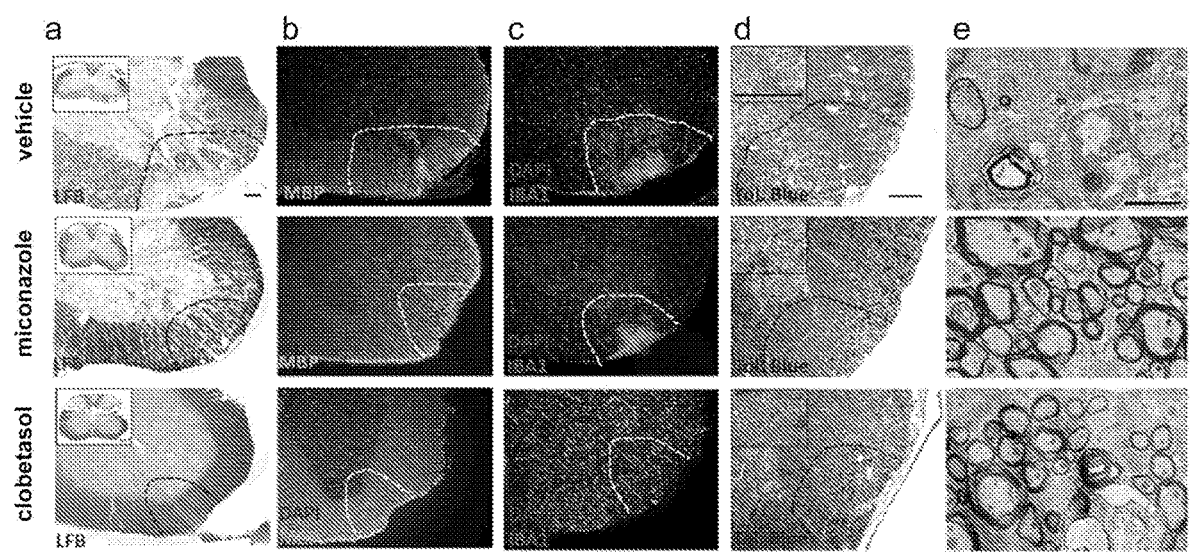
Figs. 28A-E

METHOD OF PROMOTING REMYELINATION

RELATED APPLICATIONS

This application is a Continuation of U.S. patent application Ser. No. 14/723,008, filed May 27, 2015; which is a Continuation-in-Part of International Application No. PCT/US2014/05747, filed Sep. 25, 2014; which claims the benefit of priority from U.S. Provisional Application No. 61/882,419, filed Sep. 25, 2013; U.S. Provisional Application No. 61/882,861, filed Sep. 26, 2013; and U.S. Provisional Application No. 62/003,109, filed May 27, 2014, the subject matter of each of which is incorporated herein by reference in its entirety.

GOVERNMENT FUNDING

This invention was made with government support under Grant No. CON119651 awarded by the Myelin Repair Foundation. The United States government has certain rights to the invention.

BACKGROUND

Multiple sclerosis (MS) is a complex neurological disease characterized by deterioration of central nervous system (CNS) myelin. This insulating material, composed in its majority by lipids (70% lipids, 30% protein), protects axons and makes possible the saltatory conduction, which speeds axonal electric impulse. Demyelination of axons in chronic MS may result in axon degeneration and neuronal cell death, but more specifically, MS destroys oligodendrocytes, the highly specialized CNS cells that generate and maintain myelin.

Oligodendrocyte precursors (PDGFRα+, NG2-proteoglycan+), the immature oligodendrocytes, are generated in ventral areas of the developing brain from a common glial progenitor, actively migrate and proliferate populating the CNS to finally differentiate to premyelinating oligodendrocytes (O4+). At this maturation point, oligodendrocytes both target and extend myelin sheaths along axons or they die. Less explored has been however, the hypothesis of remyelination by either endogenous oligodendrocyte precursors or transplanted cells.

Oligodendrocyte progenitor cells are abundant in demyelinated regions of patients with multiple sclerosis, yet fail to differentiate. Promoting remyelination by inducing differentiation and/or maturation of endogenous oligodendrocyte progenitors can stimulate and enhance intrinsic, natural remyelination thus reduction of clinical severity of myelination related disorders. Therefore, there is a need for compounds and therapeutic methods capable inducing endogenous oligodendrocyte precursor differentiation.

SUMMARY

Embodiments described herein generally relate to compounds and methods for promoting remyelination in a subject in need thereof as well as to methods for the treatment of disease in subjects where myelination and/or remyelination by the induction of endogenous oligodendrocyte precursor differentiation is beneficial to the subject.

In some embodiments a method of promoting remyelination in a subject in need thereof is provided. The method includes administering to the subject a therapeutically effective amount of at least one (1,3) Diazole compound, wherein the therapeutically effective amount is the amount effective to induce endogenous oligodendrocyte precursor cell (OPC) differentiation in the subject's central nervous system. In some embodiments, the at least one (1,3) diazole compound or analog thereof having the formula (I):

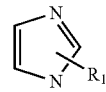

where $R_1$ is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, or pharmaceutically acceptable salts thereof.

Another embodiment relates to a method of treating a neurodegenerative disease in a subject in need thereof. The method includes administering to the subject a therapeutically effective amount of at least one (1,3) Diazole compound, wherein the therapeutically effective amount is the amount effective to induce endogenous oligodendrocyte precursor cell (OPC) differentiation and promote myelination in the subject's central nervous system. In some embodiments, the at least one (1,3) diazole compound or analog thereof having the formula (I):

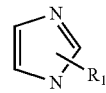

where $R_1$ is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, or pharmaceutically acceptable salts thereof.

Other embodiments relate to a method of treating a myelin related disorder in a subject in need thereof. The method includes administering to the subject a therapeutically effective amount of at least one (1,3) Diazole compound, wherein the at least one (1,3) diazole compound or analog thereof having the formula (I):

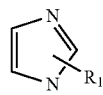

where $R_1$ is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, or pharmaceutically acceptable salts thereof, and wherein the therapeutically effective amount is the amount effective to induce endogenous oligodendrocyte precursor cell (OPC) differentiation and promote myelination in the subject's central nervous system.

BRIEF DESCRIPTION OF THE DRAWINGS

FIGS. 1(A-E) illustrate a pluripotent stem cell-based phenotypic screening platform to identify modulators of OPC differentiation and maturation. (A), Flow diagram depicting organization of primary screen as well as validation of putative drug hits. (B), RNAseq expression data showing down regulation of pluripotent stem cell transcripts and up regulation of OPC transcripts when EpiSCs are differentiated into OPCs. Fragments per kilobase exon per million reads (FPKM) for each transcript are shown as compared to in vivo isolated OPCs. (C), Representative images of vehicle and small molecule hit treated OPCs from the primary screen. Nuclear (DAPI) and myelin basic protein (MBP) staining along with high content analysis (HCA) to identify oligodendrocyte nuclei and MBP+ processes. Scale bar 100 μm. (D), Primary screen results displayed as normalized values of MBP process length and MBP process intensity for all 727 drugs. Baseline (vehicle) was set at 0 and thyroid hormone (positive control) was set at 100. The 21 drug hits were greater than 5 standard deviations above baseline. (E), Chart ranking the 21 primary drug hits into 4 tiers based on calculation of half maximal effective concentration (EC50) and 50% toxicity (50% Tox) dose calculated from 7 point dose treatment of OPCs.

FIGS. 2(A-D) illustrate four validated drugs promote precocious MBP+ axonal ensheathment in ex vivo organotypic cerebellar slice cultures. (A), Flow diagram depicting organization of cerebellar slice assay and validation by western blot. (B), Example of MBP staining of a mouse P7 cerebellar slice treated with drug for 5 days along with high content analysis (HCA) to identify aligned MBP+ fibers. Scale bar 100 μm. (C), Chart ranking 11 drugs from the primary screen into 3 groups (High, Medium, Low) based on their ability to increase MBP+ axonal ensheathment relative to vehicle (DMSO) treated controls as measured by HCA. n=6-12 medial cerebellar slices per drug. Primary screen tier classification from FIG. 1 are repeated for comparison; green (Tier A), (Tier B), and (Tier C). (D), Validation of HCA of drug treated cerebellar slices by western blot. Shown are fold changes in MBP levels for 4 drugs compared to vehicle (DMSO) treated controls.

FIGS. 3(A-E) illustrate miconazole and clobetasol reduce disease severity and promote remyelination in chronic MOG35-55 EAE mouse model. (A), Flow diagram depicting organization of EAE experimental design and analysis of five drugs. A clinical scoring system where 1=limp tail; 2=paralysis of one hind limb; and 3=paralysis of both hind limbs was employed. Mice were treated with drug or vehicle at peak of disease (~day 15 after immunization; score of 3). (B), Three drugs showed significant reduction of EAE clinical scores after 10 days of treatment in an initial treatment cohort (n=6 mice per group). (C) and (D). These three drugs were repeated for further validation with a larger treatment cohort (n=12 to 18 mice per group). The average clinical scores (C) and cumulative clinical scores (D) of miconazole and clobetasol treated animals showed significant reduction of disease and functional improvement. (E), Miconazole and clobetasol treated animals showed improvements in white matter histology compared to vehicle treated controls. Representative images of luxol fast blue (LFB) staining showed a clear decrease in areas of white matter disruption in the spinal cords of drug treated animals which coincides with increased MBP staining. IBA1 staining showed a small reduction but not an abrogation of immune cell infiltration into the lesion areas. Representative toluidine blue stained images and electron micrographs revealed areas of significant remyelination in drug treated animals. Lesioned areas are outlined with dotted lines. Insets in toluidine blue staining show higher magnification of myelination in the corresponding spinal cords. *p<0.05, **p<0.01. Arrow in C, indicates beginning of drug treatment at disease peak and error bars are standard deviation of mean. (E) Scale bar 100 μm, electron micrograph scale bar 2 μm. (B and C) Values are mean±SEM. (D) Dots each represent an individual animal with group mean (horizontal line), SD (box), and range (vertical line) depicted.

FIGS. 4(A-F) illustrate miconazole and clobetasol function through pathways conserved in mouse OPC development and in human OPCs. (A), Overview of four orthogonal assays applied to clobetasol and miconazole. (B), MBP immunohistochemistry showing corpus callosum (CC) of P7 pups treated for four days with drug or vehicle. Clobetasol and miconazole showed a significant increase in the length of the CC stained with aligned MBP+ fibers. *p<0.01, Striatum is marked as Str. (C), Representative phase contrast image of hESC colony cultured on matrigel. (D), Representative phase contrast image of hESC-derived OPCs. (E), hESC-derived OPCs stain positive for Sox10. (F), Representative images of hES-derived OPCs treated with vehicle (DMSO) or miconazole or clobetasol for 7 days. PLP staining is shown in green (top) along with high content analysis (HCA; bottom) to identify oligodendrocyte nuclei and PLP+ processes. (B, C, E, and F) Scale bars 100 µm. (D) Scale bar 50 µm. (B) Values are mean±SEM.

FIGS. 5(A-C) illustrate in vitro phenotypic screen assay development. (A), Two epiblast stem cell (EpiSC)-derived oligodendrocyte progenitor cell (OPC) batches of greater than 100 million cells were generated and used for this study. These batches were derived from independent EpiSC lines of distinct mouse strain and opposite gender. (B), The batches of EpiSC-derived OPCs were sorted to purity (circled areas of FACS plots) using OPC cell surface markers NG2 and CD140α prior to use in this study. (C), DMSO (v/v) tolerance of EpiSC derived-OPCs in 96-well plates. (n=16 wells each condition; 16 20× fields sampled/well; mean±SEM). For reference, 0.05% (v/v) DMSO was used as vehicle for all in vitro experiments in this study.

FIGS. 6(A-D) illustrate performance of the primary screen of 727 hits on 10 assay plates. (A), Thyroid hormone (positive control) and DMSO vehicle treatments yielded a consistent number of live cells imaged per well across all 10 assay plates. Values are mean±SEM. (B), Signal to background (S/B) mean values with standard deviation (s.d.) of the entire screen were within an acceptable range to enable identification of primary hits. (C), Raw data of myelin basic protein (MBP) process length from the primary screen for thyroid hormone treatment and DMSO vehicle. (D), Raw data of MBP process intensity from the primary screen for thyroid hormone treatment and DMSO vehicle. (C and D) Values are mean±SD. (A-D) 30,000 cells were seeded per well and approximately ⅓ of each well (n=8 wells each condition; 24 10× fields sampled/well) imaged yielding close to 10,000 cells sampled per well.

FIGS. 7(A-B) illustrate the dose response of miconazole. (A), Representative images of miconazole treated OPCs in dose response along with thyroid hormone (positive control) and vehicle (DMSO). Slight toxicity and a decrease in PLP1 positive cells was observed only at the highest 6.7 µM dose. Scale bar 100 µm. (B), Seven point dose response curve generated through script analysis of percent PLP1+ cells. Mean±SEM plotted.

FIGS. 8(A-B) illustrate the dose response of clobetasol. A, Representative images of clobetasol treated OPCs in dose response along with thyroid hormone (positive control) and vehicle (DMSO). Scale bar 100 µm. B, Seven point dose response curve generated through script analysis of percent PLP1+ cells. Mean±SEM plotted.

FIGS. 11(A-B) illustrate specificity of drug induced differentiation. (A), Representative images of OPCs treated with miconazole or clobetasol to evaluate drug induced astrocyte differentiation. Addition of both LIF and BMP served as a positive control. (B), Percent of astrocytes relative to dose response 6.7, 5, 3.3, 1.7, 0.7, 0.5, 0.3 µM of each drug. Positive control (+) is LIF and BMP treatment of OPCs to induce astrocyte differentiation (n=4 wells each condition; 14 20× fields sampled/well; mean±SEM). Scale bar 100 µm.

FIGS. 12(A-D) illustrate RNAseq on drug treated OPCs. (A), Volcano plots of all genes from OPCs treated with clobetasol or miconazole relative to vehicle control, with differentially expressed genes highlighted (red). Significance (measured as −log 10[qvalue]) is plotted in relationship to expression change (log 2[treatment/vehicle]). Time course was after 2, 6 and 12 hours of drug treatment. (B), Venn diagrams depicting the overlap of genes differentially expressed at any time point and increased in treatments vs vehicle (left), as well as those decreased in treatments vs vehicle (right). (C), Canonical pathways perturbed by each drug treatment according to Ingenuity Pathway Analysis. (D), Concurrent with RNAseq experiments, parallel drug treated cultures were allowed to mature into oligodendrocytes for 3 days in 12-well plates and analyzed to confirm drug efficacy in these experiments. n=3 wells each condition; 45 10× fields sampled/well; mean±SEM.

FIG. 13 illustrates NIH Clinical Collection imidazole structure activity relationship based on EAE validated hit miconazole. Primary screen rank out of 727 drugs (average of both length and intensity parameters), in parentheses. All drugs tested at 5 µM. Imidazole structure used for search [(1,3) diazole or (1,2,4)Triazole] highlighted.

FIG. 14 illustrates NIH Clinical Collection steroid structure activity relationship based on EAE validated hit clobetasol. Primary screen rank out of 727 drugs (average of both length and intensity parameters), in parentheses. All drugs tested at 5 µM. Steroid structure used for search is highlighted.

FIGS. 15(A-F) illustrate a pluripotent stem cell-based phenotypic screening platform to identify modulators of OPC differentiation and maturation. (A) Representative images of vehicle- and drug-hit-treated mouse EpiSC-derived OPCs from the primary screen. Nuclear (DAPI (4′,6-diamidino-2-phenylindole), blue) and MBP (red) staining along with HCA to identify oligodendrocyte (oligo.) nuclei (green) and MBP+ processes (yellow). Scale bar, 100 µm. (B) Scatter plot of primary screen results displayed as normalized values of MBP process length and intensity for all 727 drugs with the 22 hits marked in red. Baseline (vehicle) was set at zero and thyroid hormone (positive control) was set at 100. (C) Montaged images of whole postnatal day 7 mouse cerebellar slices treated with drug or vehicle for 5 days and stained for MBP (green). Insets show a representative example of the HCA script used to identify and quantify MBP+-aligned fibres (light blue). Scale bars, 1 mm for whole slices and 100 µm for insets. (D) Relative quantification of HCA and western blot data from cerebellar slices treated for 5 days. For HCA screen, n=1 with 6-12 slices averaged per group. For western blot, n=3 independent replicates of 12 slices per group. Values are mean for HCA and mean±s.e.m. for western blot. (E) Representative western blot of MBP isoforms and β-actin (loading control) of cerebellar slices treated for 5 days. (F) Chemical structures of clobetasol and miconazole.

FIGS. 16(A-D) illustrate miconazole and clobetasol each enhance remyelination in the LPC lesion mouse model. (A) Representative immunohistochemical images of treated mice showing newly generated oligodendrocytes (CC1, red)

Figure 9:
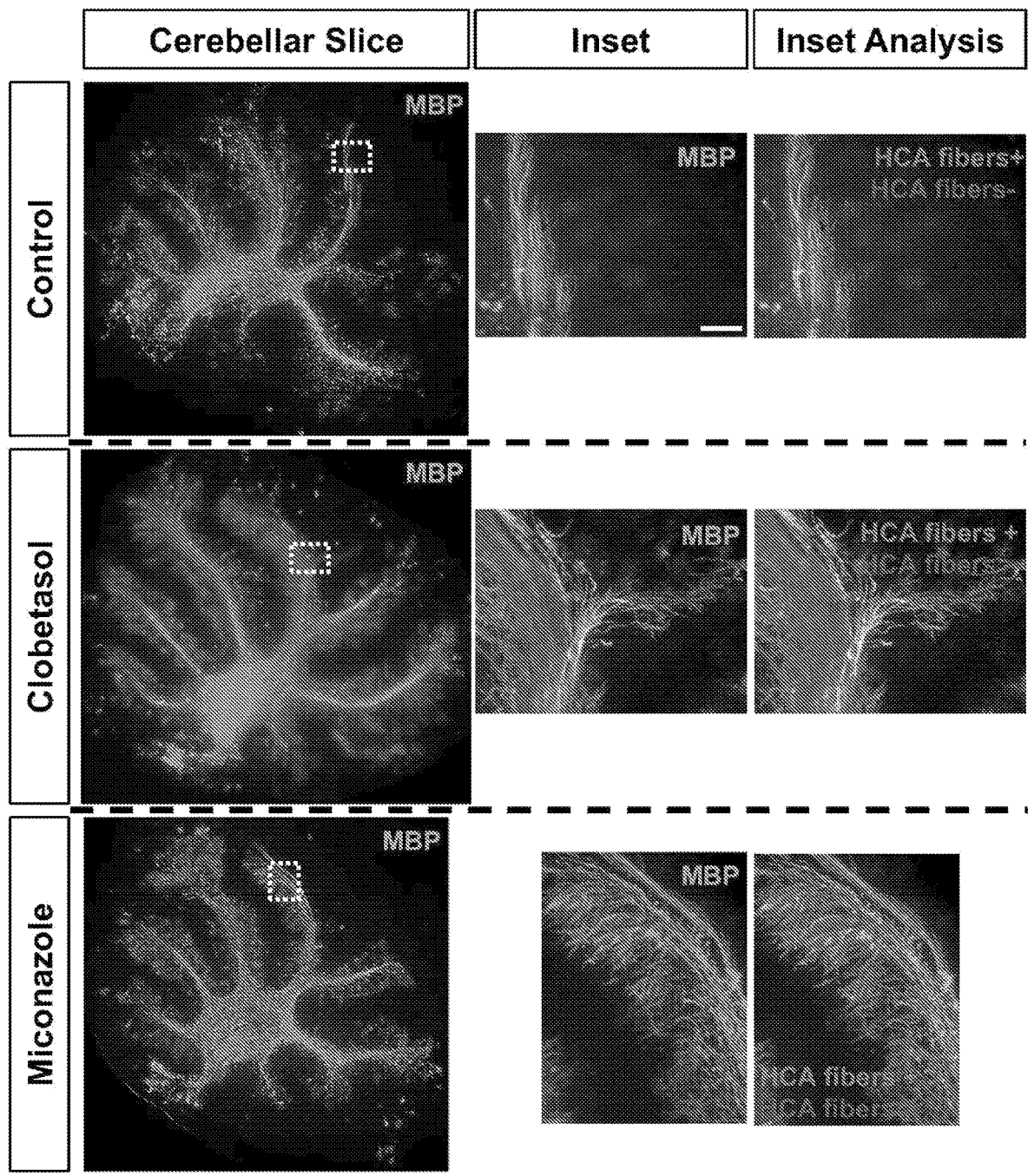
FIG. 9 illustrates high content imaging analysis of drug treated cerebellar slices. Montaged images of postnatal day 7 mouse cerebellar slices treated with drug or vehicle for 5 days and stained for myelin basic protein (MBP). Insets are a single field and inset analysis represents script identification and texture analysis of MBP positive aligned fibers. Representative MBP-stained areas called and included in script analysis. Scale bar 100 µm.

and MBP (green) within the lesion (approximated by white dashed outline) at eight and 12 d.p.l. Scale bar, 200 μm. (B) Quantification of CC1+ oligodendrocytes per lesion area at 8 d.p.l. Values are mean±s.e.m.; n=3 mice per group. Two-tailed t-test, *P<0.05. (C) Representative electron micrographs showing remyelinated axons within lesions of drug-treated mice at 12 d.p.l. Scale bar, 2 μm. (D) Scatter plot of g ratios of lesion axons at 12 d.p.l.; n=100 calculated from two mice per group compared to wild-type intact axons. Percentage of lesion axons myelinated is indicated in the legend.

FIGS. 17(A-H) illustrate cellular and molecular effects of miconazole and clobetasol on mouse OPCs. (A) Percentage MBP+ oligodendrocytes generated from OPCs at 72 h with treatments initiated at time points indicated; n=6 wells per condition with >6,000 cells scored per well. (B) Percentage MBP+ oligodendrocytes generated from OPCs treated simultaneously and analyzed at time points indicated; n=8 wells per condition with >1,700 cells scored per well. (C) Percentage GFAP+ astrocytes generated from OPCs at 72 h of treatment; n=4 wells per condition >2,900 cells scored per well. (D) Heat map depicting biochemical inhibition of muscarinic receptors M1-M5 displayed as percentage inhibition with minimum (green) and maximum (red). (E) Western blot of total glucocorticoid receptor and its phosphorylation at Ser220 (p-GR) in OPCs treated for 1 h. (F) Percentage MBP+ oligodendrocytes generated from OPCs 72 h after treatment; n=6 wells per condition with >1,400 cells scored per well. (G) Western blot of total ERK1/2 and their phosphorylation at Thr202/Tyr204 or Thr185/Tyr187 (p-ERK1/2) in cells (OPCs or mouse embryonic fibroblasts) treated for 1 h. FGF served as a positive control for p-ERK1/2 induction. (H) Western blot of total ERK1/2 and p-ERK1/2 in OPCs treated for 1 h in the presence of the indicated pathway inhibitors. All graphs depict mean±s.e.m.

FIGS. 18(A-D) illustrate the therapeutic efficacy of miconazole and clobetasol in mouse models of MS. (A) Scoring of disease severity in relapsing remitting PLP$_{139-151}$⁻ induced EAE mice treated beginning on day 13 (black arrow) and ending on day 29; n=10 mice per group. Graph depicts mean daily disease score±s.e.m. (B) Flow-cytometric-based quantification of spleen cell numbers at day 29 from the PLP$_{139-151}$ EAE cohort in A. Values are mean±s.e.m.; n=4 or 5 mice per group. (C) Scoring of disease severity in chronic progressive MOG$_{35-55}$⁻ induced EAE mice treated daily for 10 days beginning at the peak of disease on day 15 (black arrow); n=12-16 mice per group. Graph depicts mean daily disease score±s.e.m. (D) Mean improvement in disease score per animal (peak score minus ending score) of MOG$_{35-55}$ EAE cohort in C. Also shown are external validation results in MOG$_{35-55}$ EAE from an independent contract laboratory. n=12 mice per group. For all EAE experiments, drugs were dosed daily by intraperitoneal injection: clobetasol (2 mg/kg), miconazole (10 mg/kg), benztropine (10 mg/kg), or FTY720 (1 mg/kg). All EAE disease scoring was as follows: 0, no abnormality; 1, limp tail; 2, limp tail and hind limb weakness; 3, hind limb paralysis; 4, hind limb paralysis and forelimb weakness; and 5, moribund. Two-tailed t-test, *P<0.05 and **P<0.01 for drug-treated groups compared with their respective vehicle-treated group.

FIGS. 19(A-G) illustrate the performance of the primary screen. (A) Representative flow cytometry plots showing co-expression of NG2 and CD140a in both batches of EpiSC-derived OPCs used for this study. The batches of EpiSC-derived OPCs were sorted to purity (circled areas of plots) before use in this study. (B) RNaseq expression heat map showing downregulation of pluripotent stem cell transcripts and upregulation of OPC transcripts when EpiSCs were differentiated into OPCs. Fragments per kilobase exon per million reads (FPKM) for each transcript are shown compared with in vivo isolated mouse OPCs. (C) Quantification of DMSO (v/v) tolerance of EpiSC derived OPCs in 96-well plates shown as mean±s.e.m. For reference, 0.05% (v/v) DMSO was used as vehicle for all in vitro experiments in this study; n=16 wells per group with >690 cells scored per well. (D) Quantification of cell viability of thyroid hormone (positive control) and DMSO vehicle treatments per well across all ten assay plates shown as mean±s.e.m.; n=80 wells per group with >6,800 cells scored per well. (E) Signal to background (S/B) mean values with standard deviation (s.d.) of controls from the entire screen; n=80 wells per group. (F) Raw data of MBP process length from the primary screen for thyroid hormone treatment and DMSO vehicle across all plates shown as mean±s.d.; n=8 wells per group with >6,800 cells scored per well. (G) Raw data of MBP process intensity from the primary screen for thyroid hormone treatment and DMSO vehicle shown as mean±s.d.; n=8 wells per group with >6,800 cells scored per well.

FIGS. 20(A-B) illustrate drag hit making and validation. (A) Chart ranking the 22 primary drug hits (single dose rank) into four tiers on the basis of calculation of EC$_{50}$ to induce PLP1+ oligodendrocytes from OPCs and the concentration at which 50% of the cells were lost (50% Tox) calculated from a seven-point dose treatment; n=4 wells per dose per drug using independently sourced drug and separate OPC batch from the primary screen. Tiers ranged from the most potent and least toxic effectors to the least potent and most toxic: tier a (green), tier b (grey), tier c (orange), and tier d (red). The 1,536-well format external validation of 14 out of 16 tested hits is also shown. Drugs were further ranked into groups of high (green), medium (grey), and low (orange) on the basis of their ability to increase MBP+ axonal ensheathment in mouse cerebellar brain slices relative to vehicle (DMSO)-treated controls as measured by HCA. NT, not tested. (B) External validation whole 1,536-well images of MBP+ (green) oligodendrocytes generated from OPCs after 72 h of treatment. GE InCell HCA is shown with processes traced in yellow and nuclei in blue.

FIGS. 21(A-D) illustrate primary screen structure-activity analysis. Chemoinformatic identification of two substructures consistently enriched in high-performing drugs in the OPC assay. Numerical activity rank in the primary screen is indicated with the top 22 shown in green, 23-50 shown in grey, and 0.51 in red. (A) 1,3-Diazoles, mono-substituted at the 1-position showed consistent activity on OPCs. b, c, 1,3-Diazoles, poly-substituted at two or more of the R groups (B) or 1,2,4-triazoles, mono-substituted at the 1-position (C) showed no activity on OPCs. (D) The sterane base structure showed enrichment in the top performing hits.

FIGS. 22(A-B) illustrate histological assessment of remyelination in the LPC-induced model of demyelination. (A) Representative electron micrographs showing remyelinated axons within lesions of miconazole treated mice at 8 d.p.l. Scale bar, 2 mm. (B) Histological sections stained with toluidine blue showing the extent of remyelination in the lesions of treated animals at 12 d.p.l. Normal uninjured myelin appears to the left of the black dashed line demarcating the definitive lesion edge. Scale bar, 20 mm.

FIGS. 23(A-B) Miconazole and clobetasol enhance myelination in vivo. (A) (B) Representative immunohistochemical images of the lateral corpus callosum (CC) of postnatal day 6 mouse pups that had been injected intraperitoneally daily for 4 days previously starting on postnatal day 2 with vehicle, clobetasol (2 mg/kg), or miconazole (10 mg/kg). CC1 (red) marks newly generated oligodendrocytes (a) and MBP (green) shows the extent of developmental myelination (b). Clobetasol and miconazole treatment each induce a marked increase in the number of CC1-positive oligodendrocytes in the lateral corpus callosum (A) and a significant increase in the length of the corpus callosum covered with aligned MBP$^+$ fibres (B). Scale bar, 200 mm. Twotailed t-test, *P≤0.05 and **P≤0.01. Str, striatum. All graphs are presented as mean±s.e.m.

FIGS. 24(A-C) illustrate RNaseq time course of drug-treated OPCs. (A) Volcano plots of all genes from OPCs treated with clobetasol or miconazole relative to vehicle control, with differentially expressed genes highlighted (red). Significance (measured as $-\log_{10}$[q value]) is plotted in relation to expression change ($\log_2$[treatment/vehicle]). Time course was after 2, 6, and 12 h of drug treatment. (B) Venn diagrams depicting the overlap of genes differentially expressed at any time point and increased in treatments versus vehicle (left), as well as those decreased in treatments versus vehicle (right). (C) Significant canonical pathways perturbed by each drug treatment according to Ingenuity Pathway Analysis.

FIGS. 25(A-C) illustrate Global phosphoproteomic analysis of miconazole-treated OPCs. (A, B) OPCs treated with miconazole for (A) 1 h or (B) 5 h followed by global phosphoproteomic analysis. Proteins highlighted in green were observed to have a twofold or greater increase in phosphorylation whereas those highlighted in red were observed to have a twofold or greater decrease in phosphorylation compared with time-point-matched vehicletreated controls. Proteins highlighted in grey were detected in the analysis but were not changed compared with vehicle control. (C) Quantification of the percentage of MBP$^+$ oligodendrocytes differentiated from mouse OPCs after 72 h of treatment with DMSO, miconazole (1 µM), or voriconazole (seven doses, 0.01-6.7 µM); n=6 wells per condition with 6,000 cells scored per well. Graph presented as mean±s.e.m. The chemical structure of voriconazole is shown.

FIGS. 26(A-G) illustrate miconazole and clobetasol enhance human OPC differentiation. (A) Representative phase contrast image of a hESC colony cultured on matrigel. (B), Representative phase contrast image of hESC-derived OPCs. (C) hESC-derived OPCs stain positive for Sox10. (D,E) Representative images of hESC-derived OPCs (d) and hiPSC-derived OPCs (e) treated with vehicle (DMSO), miconazole (1 µM), or clobetasol (5 µM) for 21 days stained for MBP (red). (F,G) HCA of hESC-derived (F) and hiPSC-derived (G) OPCs differentiated in the presence of drugs or vehicle over 21 days; n=3-5 wells per condition with >120 cells scored per well. Graphs presented as mean±s.e.m. Scale bars, 100 mm.

FIGS. 27(A-J) illustrate the effects of miconazole and clobetasol on immune cell survival and function. (A-D) Quantification of cell proliferation (A, C) and differentiation (B, D) of naive CD4$^+$ T cells from unprimed SJL/J mice after activation with plate-bound anti-CD3 under Th1 (A, B) or Th17 (C, D) cell driving conditions. (E-J) Ex vivo recall assays quantifying cell proliferation (DCPM) (E, H), with IFN-γ (F, I) and IL-17 (G, J) cytokine production from lymphocytes of mice primed with PLP$_{139-151}$ (E-G) or MOG$_{35-55}$ (H-J). Cultures were treated with vehicle (DMSO), benztropine, clobetasol, or miconazole ($10^{-9}$-$10^{-5}$ M) and analysed after 4 days. Four independent replicates are shown for each assay.

FIGS. 28(A-E) illustrate Histological improvements in MOG35-55 EAE spinal cords after treatment with miconazole or clobetasol. (A), (B) Representative images of luxol fast blue (LFB) staining (A) demonstrated a clear decrease in areas of white matter disruption in the spinal cords of drugtreated animals which coincides with increased MBP staining (B). (C) IBA1 staining showed a small reduction of immune cell infiltration into the lesion areas, especially in clobetasol-treated animals, but not an abrogation. (D, E) Representative images stained with toluidine blue (D) and electron micrographs (E) revealed a reduction in the areas of demyelination in drugtreated animals. Lesioned areas are outlined with black dotted lines. Insets in toluidine blue staining show higher magnification of myelination in the corresponding spinal cords. Scale bars, 100 mm (A-C, D) and 2 µm (E).

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular,* 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the application.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2n-1$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid OR solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, N.Y.-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. In a particular aspect, the subject is afflicted with a neurodegenerative disease or disorder. In certain aspects, the subject is afflicted with a myelination related disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent. In certain embodiments, a therapeutically effective amount is the amount effective to induce endogenous oligodendrocyte precursor cell differentiation and/or maturation, thereby promoting myelination in the subject's central nervous system.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

Embodiments described herein relate to methods of promoting remyelination in a subject in need thereof as well as treating a myelination related disorder in a subject in need thereof. Compounds described herein can be used in the treatment of myelination related neurodegenerative disorders, such as multiple sclerosis, to induce and promote differentiation and/or maturation of endogenous oligodendrocyte precursor cells, thereby promoting myelination or remyelination in some cases in the subject's central nervous system. The term "remyelination" as used herein refers to the process of creating new myelin sheaths on demyelinated axons in the CNS.

The term "oligodendrocyte precursor cells" as used herein refers immature or induced oligodendrocyte cells. Oligodendrocyte precursor cells can be identified by the expression of a number of surface antigens. For example, the surface antigens known as platelet-derived growth factor-alpha receptor subunit (PDGFRα), NG2 chondroitin sulfate proteoglycan, and ganglioside GD3, are commonly used to identify oligodendrocyte precursor cells.

Endogenous immature oligodendrocyte precursors are generated in ventral areas of the developing brain from a common glial progenitor. The immature cells actively migrate and proliferate populating the CNS to finally differentiate to premyelinating oligodendrocytes (O4+). Oligodendrocyte precursor differentiation and maturation is characterized by an extension of multiple processes, increase in cell body size and formation of myelin.

In some embodiments, the compounds for use in the methods described herein are identified using a high-throughput small molecule screen that is biased to identify compounds that have both a high potency and low toxicity in mammal subjects and are able to induce and promote differentiation and/or maturation of oligodendrocyte precursor cells or that are capable of promoting remyelination in a subject in need thereof. The term "small molecule" as used herein refers to biologically active organic compounds of low molecular weight (e.g. <500 kDa) which may cross biological membranes and modulate intracellular processes.

Briefly, the high-throughput small molecule screen can include a primary screening where small drug-like organic compounds (250-550 kDa) are added to cells seeded on a multiwall plate (e.g., 96-well plate) and incubated. The cells are then visually screened for oligodendrocyte precursor morphology changes. In a secondary screening, differentiation and maturation induced by selected compounds was further validated by fluorescence microscopy. Further oligodendrocyte precursor differentiation and maturation in response to selected compounds can be assessed by induction of myelin protein expression as determined by immunocytochemistry and western blot. Examples of assays that can be used in the primary and secondary screening are described in Najm et al. Nat Methods. 2011 Sep. 25; 8(11):957-62; Bai et al. Neurosci Bull. 2013 April; 29(2): 239-50; Yang et al. Dev Biol. 2011 Feb. 1; 350(1):127-38; and Cho et al. Curr Neuropharmacol. 2007 March; 5(1): 19-33

In some embodiments, the compounds can be further screened using a brain slice ex vivo assay that assesses myelination the brains of mammals, (e.g., rats and mice). Such assays are described, for example, in Bai et al. Neurosci Bull. 2013 April; 29(2):239-50, Yang et al. Dev Biol. 2011 Feb. 1; 350(1):127-38, and Cho et al. Curr Neuropharmacol. 2007 March; 5(1): 19-33.

In some embodiments, the compounds can be further screened using an in vivo assay that assesses remyelination and reduction of clinical severity in the $MOG_{35-55}$-induced chronic experimental autoimmune encephalomyelitis (EAE) rodent model of multiple sclerosis.

Examples of compounds identified by the high-throughput small molecule screen can include free 1,3-diazoles or free primary diazoles. In some embodiments, the free 1,3-diazoles can have the formula (I):

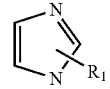

where $R_1$ is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O)$_2$), phosphinato (—P(O)(O—)), phospho (—PO$_2$), phosphino (—PH$_2$), or combinations thereof.

In some embodiments, the diazoles can include primary 1,3-diazoles such as, but not limited to, a primary 1,3-diazole having the formula:

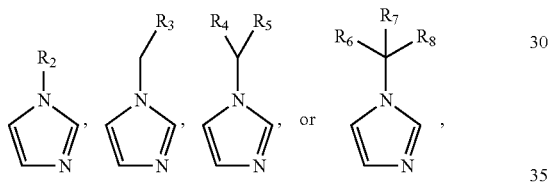

wherein R$_2$, R$_3$, R$_4$, R$_5$, R$_6$, R$_7$, and R$_8$ are each individually a substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, C$_2$-C$_{24}$ alkoxycarbonyl, C$_6$-C$_{20}$ aryloxycarbonyl, C$_2$-C$_{24}$ alkylcarbonato, C$_6$-C$_{20}$ arylcarbonato, carboxy, carboxylato, carbamoyl, C$_1$-C$_{24}$ alkyl-carbamoyl, arylcarbamoyl, thiocarbamoyl, carbamido, cyano, isocyano, cyanato, isocyanato, isothiocyanato, azido, formyl, thioformyl, amino, C$_1$-C$_{24}$ alkyl amino, C$_5$-C$_{20}$ aryl amino, C$_2$-C$_{24}$ alkylamido, C$_6$-C$_{20}$ arylamido, imino, alkylimino, arylimino, nitro, nitroso, sulfo, sulfonato, C$_1$-C$_{24}$ alkylsulfanyl, arylsulfanyl, C$_1$-C$_{24}$ alkylsulfinyl, C$_5$-C$_{20}$ arylsulfinyl, C$_1$-C$_{24}$ alkylsulfonyl, C$_5$-C$_{20}$ arylsulfonyl, phosphono, phosphonato, phosphinato, phospho, or phosphino.

In certain specific embodiments, R$_2$, R$_3$, R$_4$, R$_5$, R$_6$, R$_7$, and R$_8$ are each individually one or more substituted or unsubstituted groups selected from:

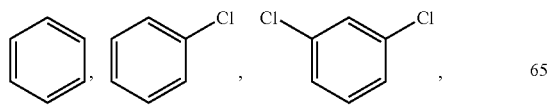

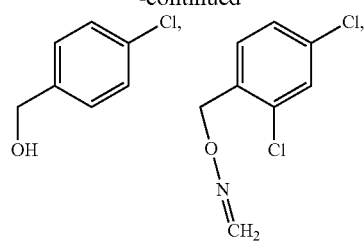

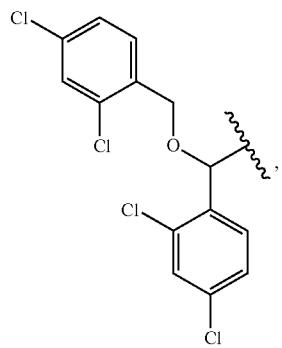

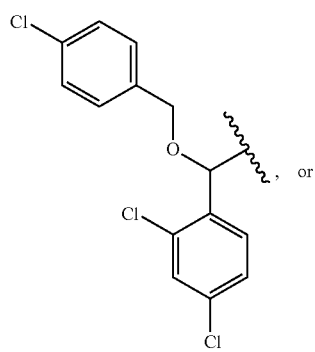

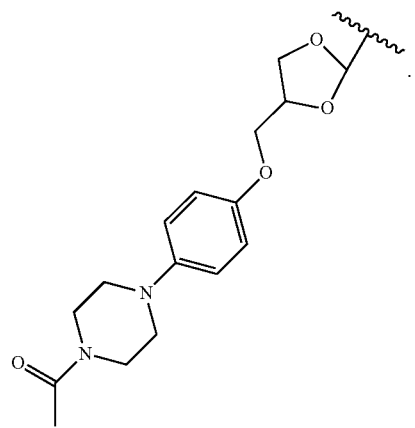

Certain specific embodiments of Formula (1) are shown below:

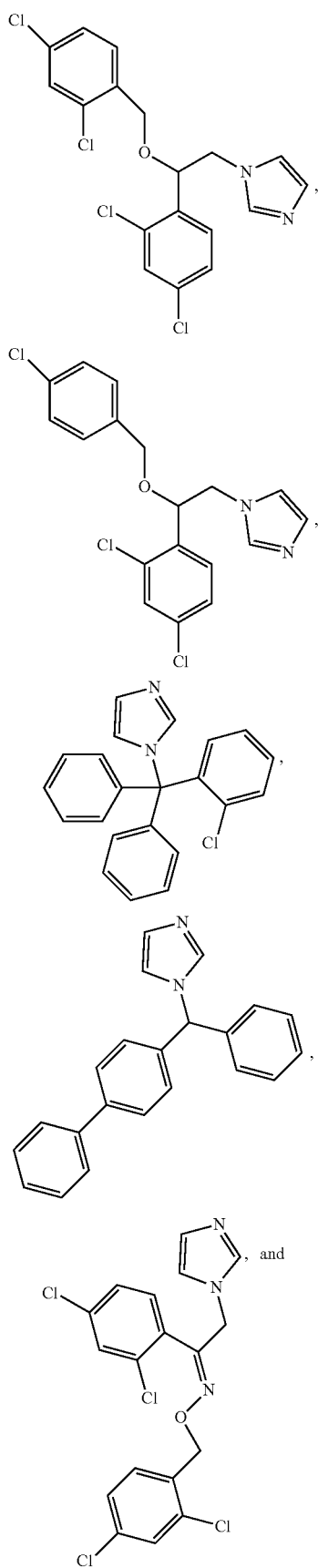

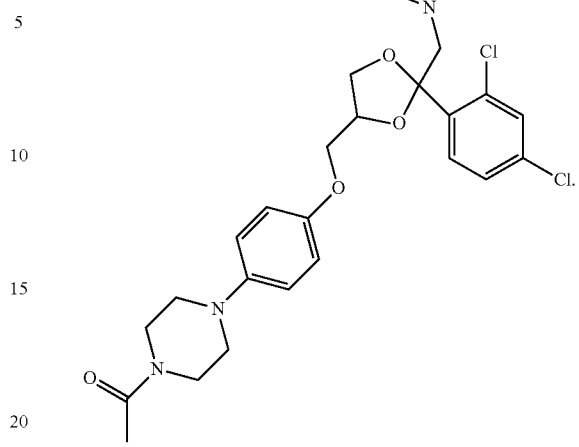

Compounds described herein may be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting material used for the synthesis of compounds described herein can be obtained from commercial sources, such as Aldrich Chemical Co. (Milwaukee, Wis.). Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety).

In accordance with one aspect of the invention, a method of promoting remyelination in a subject in need thereof is provided. The method includes administering to the subject a therapeutically effective amount of at least one free (1,3) diazole compound or free primary diazole, wherein the therapeutically effective amount is the amount effective to induce endogenous oligodendrocyte precursor differentiation and/or maturation in the subjects central nervous system.

The oligodendrocyte precursor cell differentiation and/or maturation promoting compounds can be provided and administered in the form of pharmaceutical compositions for the in vivo promotion of oligodendrocyte precursor differentiation and/or maturation. The pharmaceutical compositions can be administered to any subject that can experience the beneficial effects of the oligodendrocyte precursor differentiation and/or maturation compounds of the present invention. Foremost among such animals are humans, although the present invention is not intended to be so limited.

Pharmaceutical compositions for use in the methods of the present invention preferably have a therapeutically effective amount of the compound or salts thereof in a dosage in the range of 0.01 to 1,000 mg/kg of body weight of the subject, and more preferably in the range of from about 1 to 100 mg/kg of body weight of the patient. In certain embodiments, the pharmaceutical compositions for use in the methods of the present invention have a therapeutically effective amount of the compound or salts thereof in a dosage in the range of 1 to 10 mg/kg of body weight of the subject.

The overall dosage will be a therapeutically effective amount depending on several factors including the particular compound used, overall health of a subject, the subject's disease state, severity of the condition, the observation of improvements, and the formulation and route of administration of the selected agent(s). Determination of a therapeutically effective amount is within the capability of those skilled in the art. The exact formulation, route of administration and dosage can be chosen by the individual physician in view of the subject's condition.

The present invention also provides a method of treating a neurodegenerative disease or disorder in a subject in need thereof by inducing endogenous oligodendrocyte precursor cell (OPC) differentiation and promote myelination in the subject's central nervous system. The method includes administering to the subject in need thereof a therapeutically effective amount of a (1,3) Diazole compound in accordance with the present invention. As described above, one or more of the compounds can be administered in association with one or more non-toxic, pharmaceutically acceptable carriers and/or diluents and/or adjuvants and if desired other active ingredients.

The "therapeutically effective amount" of compounds and salts thereof used in the methods of the present invention varies depending upon the manner of administration, the age and body weight of the subject, and the condition of the subject to be treated, and ultimately will be decided by those skilled in the art. The term "therapeutically effective amount" refers to an amount (dose) effective in treating a subject, having, for example, a neurodegenerative disease (e.g. multiple sclerosis).

In some embodiments, the therapeutically effective amount is the amount effective to induce endogenous oligodendrocyte precursor cell (OPC) differentiation and/or maturation and thereby promote myelination in the subject's central nervous system. The induction of endogenous oligodendrocyte precursor cell (OPC) differentiation can be characterized by a significant increase of myelin basic protein (MBP) expression in newly generated mature myelinating oligodendrocytes in a subject. For example, the increase of MBP expression can be an increase of MBP expression greater than about 50%, about 100% or about 150% or more. In certain embodiments, the increase of MBP expression is greater than 150% or more compared to a control. In some embodiments, a control value can be readily determined by measuring the MBP expression in a subject's demyleniated lesion prior to administration of a pharmaceutical composition described herein.

Differentiated and/or mature oligodendrocytes can be identified by the oligodendrocyte cell body marker CC1 as opposed to the myelinated processes identified using MBP expression. Thus, in some embodiments, the therapeutically effective amount is the amount effective to generate CC1$^+$ oligodendrocytes in the subject's central nervous system, particularly in a subject's demyelinated lesion site.

It has been shown that genetic loss of ERK1/2 in the oligodendrocyte lineage results in normal numbers of OPCs and oligodendrocytes but widespread hypomyelination, while constitutive activation of ERK1/2 results in a profound increase in the extent of remyelination after toxin-induced demyelinating injury. Thus, in some embodiments, the therapeutically effective amount is the amount effective to induce EKR1/2 phosphorylation and activation in OPCs of the subject.

"Treating" or "treatment" as used herein, refers to the reduction in severity and/or frequency of symptoms, elimination of symptoms and/or underlying cause, prevention of the occurrence of symptoms and/or their underlying cause, and improvement or remediation of disease. Such treatment need not necessarily completely ameliorate the disease. For example, treatment of a subject with a neurodegenerative disease by administration of oligodendrocyte precursor differentiation compounds of the present invention can encompass inhibiting or causing regression of the disease. Further, such treatment can be used in conjunction with other traditional treatments for neurodegenerative diseases known to those of skill in the art.

The pharmaceutical compositions of the present invention can be administered to a subject by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route.

Formulation of the pharmaceutical compounds for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. Compounds of the invention can be formulated into pharmaceutical compositions containing pharmaceutically acceptable non-toxic excipients and carriers. The excipients are all components present in the pharmaceutical formulation other than the active ingredient or ingredients. Suitable excipients and carriers useful in the present invention are composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

The compounds can be administered to a subject to treat neurodegenerative conditions in subjects in need thereof. A neurodegenerative disease, as contemplated for treatment by methods of the present invention, can arise from but is not limited to stroke, heat stress, head and spinal cord trauma (blunt or infectious pathology), and bleeding that occurs in the brain. Examples of neurodegenerative disorders contemplated include Alexander disease, Alper's disease, Amyotrophic lateral sclerosis, Ataxia telangiectasia, Spielmeyer- Vogt-Sjogren-Batten disease, Bovine spongiform encephalopathy, Canavan disease, Cockayne syndrome, Corticobasal degeneration, Creutzfeldt-Jakob disease, Huntington's Disease, HIV-associated dementia, Kennedy's disease, Krabbe disease, Lewy body dementia, Spinocerebellar ataxias, Multiple Sclerosis, Multiple system atrophy, Neuroborreliosis, Parkinson's disease, Pelizaeus-Merzbacher disease, Pick's disease, Primary lateral sclerosis, Prion diseases, Refsum's disease, Sandhoff disease, Schilder's disease, Spinal muscular atrophy, Steele-Richardson-Olszewski disease, and tabes dorsalis.

The neurodegenerative disease contemplated for treatment by some aspects of the present invention can include a myelin related disorder. Myelin disorders can include any disease, condition (e.g., those occurring from traumatic spinal cord injury and cerebral infarction), or disorder related to demylination, remylination, or dysmyelination in a subject. A myelin related disorder as used herein can arise from a myelination related disorder or demyelination resulting from a variety of neurotoxic insults. "Demyelination" as used herein, refers to the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy, and Guillain-Barre Syndrome. Leukodystrophies are caused by inherited enzyme deficiencies, which cause abnormal formation, destruction, and/or abnormal turnover of myelin sheaths within the CNS white matter. Both acquired and inherited myelin disorders share a poor prognosis leading to major disability. Thus, some embodiments of the present invention can include methods for the treatment of neurodegenerative autoimmune diseases in a subject. The term "remyelination", as used herein, refers to the re-generation of the nerve's myelin sheath by replacing myelin producing cells or restoring their function.

One particular aspect of the present invention contemplates the treatment of multiple sclerosis in a subject. The method includes administering to the subject a therapeutically effective amount of one or more oligodendrocyte differentiation promoting compound(s) described above.

Multiple sclerosis (MS) is the most common demyelinating disease. In multiple sclerosis, the body's failure to repair myelin is thought to lead to nerve damage, causing multiple sclerosis associated symptoms and increasing disability. It is contemplated that methods of the present invention can promote oligodendrocyte precursor cell differentiation in a subject, therefore leading to endogenous remyelination.

Another strategy for treating a subject suffering from a neurodegenerative disorder such as a myelination related disorder is to administer a therapeutically effective amount of a free 1,3-diazole or free primary diazole compound described herein along with a therapeutically effective amount of additional oligodendrocyte differentiation and/or proliferation inducing agent(s) and/or anti-neurodegenerative disease agent. Therefore, in a further aspect of the invention, the 1,3-diazole or free primary diazole oligodendrocyte precursor differentiation and/or proliferation inducing agents can be administered as part of a combination therapy with adjunctive therapies for treating neurodegenerative and myelin related disorders.

For example, therapeutic methods described herein can further comprise administering to the subject at least one additional oligodendrocyte differentiation and/or proliferation inducing agent(s) having the formula (II). Compounds having the formula (II) can be identified by the high-throughput small molecule screen described above and can include compounds having a sterane base such as a steroid hormone or analog thereof. In some embodiments, the sterane base compound can have the formula (II):

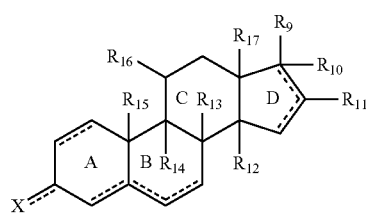

where (a) $R_9$, $R_{10}$, $R_{11}$, $R_{12}$, $R_{13}$, $R_{14}$, $R_{15}$, $R_{16}$, $R_{17}$ are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof, and wherein $R_{10}$ and $R_{11}$ may be linked to form a cyclic or polycyclic ring, wherein the ring is a substituted or unsubstituted aryl, heteroaryl, cycloalkyl, or heterocyclyl;

(b) the ABCD ring structure and/or one or more methyl group are independently optionally substituted with one or more substituents selected from $C_1$-$C_6$-alkyl, halogenated $C_1$-$C_6$-alkyl, $C_1$-$C_6$-alkenyl, halogenated $C_1$-$C_6$-alkenyl, halogen, amino, aminoalkylene, hydroxyimino, carbonyl (oxo), and hydroxy;

(c) X is OH or O;

(d) dashed lines are taken at each occurrence independently to be double or single bonds; and combinations thereof, or pharmaceutically acceptable salts thereof.

In compounds of Formula (II), the ABCD ring structure is the "A", "B", "C" and "D" ring portions of a steroid or an analog thereof, which are optionally substituted; X is O-linked sulfate, OH or O; and wherein the dashed lines can be taken at each occurrence independently to be double or single bonds, such to make a valence satisfied and stable molecule.

In some embodiments, optional substituents of the ABCD ring structure include one or more of: $C_1$-$C_6$-alkyl and halogenated $C_1$-$C_6$-alkyl; $C_1$-$C_6$-alkenyl and halogenated $C_1$-$C_6$-alkenyl, including where the double bond is directly attached to the ring structure; halogen; amino; aminoalkylene; hydroxyimino; carbonyl (oxo); O-linked sulfate, and hydroxy. Hydrogen substituents on adjacent carbon atoms of the ABCD ring structure can be optionally removed and replaced by an additional bond between the adjacent carbon atoms to result in a double bond between these carbons in the ring structure. In some embodiments, optional substitutions on the ABCD ring structure are methyl groups at one or more positions of the ring structure.

Certain embodiments of Formula (II) include one or more substituent chosen independently from a hydroxy, or carbonyl (oxo), at any position of the "A", "B", "C" and "D" ring.

Certain specific embodiments of Formula (V) are shown below:

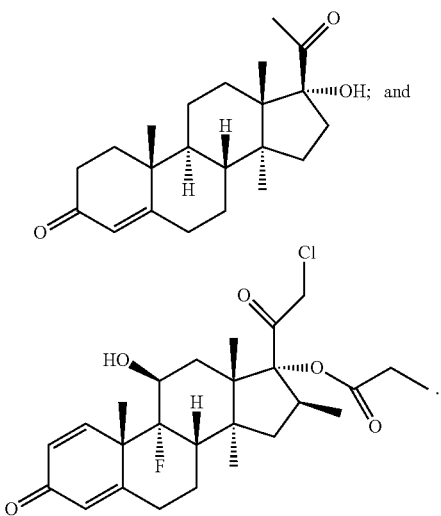

Another example of a compound identified by the high-throughput small molecule screen that can be used to promote oligodendrocyte precursor differentiation and maturation is shown below as Formula (III):

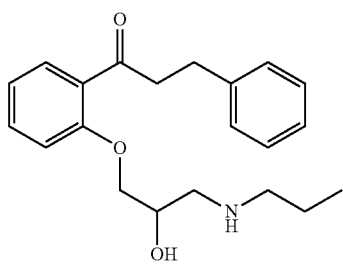

and analogs thereof.

Examples of anti-neurodegenerative disease agents for use in a combination therapy with a 1,3-diazole or free primary diazole can include L-dopa, cholinesterase inhibitors, anticholinergics, dopamine agonists, steroids, and immunomodulators including interferons, monoclonal antibodies, and glatiramer acetate.

The phrase "combination therapy" embraces the administration of the endogenous oligodendrocyte precursor differentiation inducing agents and a therapeutic agent as part of a specific treatment regimen intended to provide a beneficial effect from the co-action of these therapeutic agents. When administered as a combination, the oligodendrocyte precursor differentiation inducing agents and an additional therapeutic agent can be formulated as separate compositions. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (e.g., surgery).

In another aspect of the invention, the therapeutic agents administered in a combination therapy with the oligodendrocyte precursor cell differentiation and/or proliferation inducing agents can include at least one anti-neurodegenerative agent selected from the group consisting of an immunotherapeutic agent.

An immunotherapeutic agent for use in the methods of the present invention can include therapies which target the immune component of the disease and/or the acute inflammatory response evidenced during an acute attack in remitting-relapsing multiple sclerosis. Examples include, but are not limited to immunomodulators such as interferon beta-1a and beta-1b (Avonex and Betaseron respectively), natalizumab (Copaxone) natalizumab (Tysabri), glatiramer acetate (Copaxone) or mitoxantrone.

The following example is included to demonstrate different embodiments of the invention. It should be appreciated by those of skill in the art that the techniques disclosed in the example, which follow represent techniques discovered by the inventors to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

EXAMPLE

Drug Based Modulation of Endogenous Stem Cells Promotes Functional Remyelination in vivo.

As repair of damaged myelin may provide therapeutic benefit in multiple sclerosis (MS) and other demyelinating disorders, we set out to identify drugs that could be re-purposed as remyelinating therapeutics. We selected the US National Institutes of Health (NIH) Clinical Collection I and II libraries comprising 727 drugs with a history of safe use in clinical trials, to test for maturation of oligodendrocyte progenitor cell (OPCs) into myelinating oligodendrocytes. Using mouse epiblast stem cell (EpiSC)-derived OPCs, we developed an in vitro phenotypic screen that accurately quantified differentiation into mature oligodendrocytes by high content imaging of myelin protein expression (FIG. 1A).

Two batches (>100 million cells each) of pureOPCs were generated from independent mouse pluripotent EpiSC lines of opposite sex (FIG. 5A). EpiSC-derived OPCs shared virtually all defining molecular and cellular properties, including gene expression profiles with in vivo isolated OPCs, but provided the key advantage of being highly scalable (FIG. 5B). For in vitro screening, the seeding density, endpoint assays, and dimethylsulphoxide (DMSO) (vehicle) tolerance were optimized in pilot studies to assure accurate and reproducible measurement of OPC differentiation in a 96-well format (FIG. 5C).

For the primary screen, OPCs were treated with vehicle alone (0.05% (v/v)DMSO) as a negative control, thyroid hormone (a known OPC differentiation inducer) as a positive control, or drug dissolved in DMSO at a concentration of 5 µM. After 72 h, cells were fixed and labeled with antibodies to myelin basic protein (MBP) and the length and intensity of MBP labeled oligodendrocyte processes measured (FIG. 1A). These features were reliable indicators of alteration in cellular phenotype, as indicated by consistency and high signal to background ratio of positive and vehicle controls across all screening plates (FIG. 5D-G). We then normalized the experimental data for the tested drugs against thyroid hormone (set value of 100) on a per plate basis. On the basis of this analysis, we identified the 22 drugs that enhanced oligodendrocyte formation greater than five standard deviations above DMSO treatment and outperformed thyroid hormone in the measured parameters (FIG. 1B). Notably, one of the top 22 drugs was benztropine, a muscarinic receptor antagonist recently shown to induce OPC differentiation and remyelination.

To validate and prioritize the 22 drug hits, the assay was repeated using alternative OPCs, reagents, and parameters to eliminate screenspecific artifacts (see Methods). Drugs were ranked by their dose dependent ability to induce oligodendrocyte generation from OPCs without toxicity (FIG. 6A). To demonstrate reproducibility, an independent laboratory tested selected drug hits using distinct equipment, plate format (1,536-well), personnel, and imaging/analysis scripts (see Methods). Of the 16 hits tested at the external screening site, 14 were validated as potent inducers of oligodendrocyte differentiation (FIG. 6A, B).

We next tested whether the drug hits could promote the maturation of native OPCs in central nervous system (CNS) tissue. Cerebellar slices were generated from mice at postnatal day 7—a time that precedes widespread myelination—and treated ex vivo with drug or DMSO (vehicle) for 5 days and labeled with anti-MBP antibodies (FIG. 1C). We screened 11 of the top drugs and used a high content analysis (HCA) algorithm developed in house to rank them on the basis of their ability to increase the extent of MBP1 aligned fibres in whole cerebellar slices. The 'high' performing group consisted of four drugs that increased the number of MBP$^+$ aligned fibres ~150% or greater (FIG. 1D and FIG. 6A). We validated the accuracy of our high content screen by semi-quantitative western blotting of MBP protein isoforms in independent slice culture experiments (FIG. 1D, E).

Analysis of structure-activity relationships revealed that the top hits from the primary screen segregated into two specific classes containing either a 1,3-diazole with monosubstitution at the 1-position or a sterane base structure (FIG. 7A-D). We selected miconazole and clobetasol, the top overall performing hits in each of the imidazole and sterane classes respectively, for further mechanistic and functional testing after confirming that both drugs readily crossed the blood-brain barrier in mice (FIG. 1F and FIG. 6A). Miconazole is a topical antifungal agent functioning through cytochrome P450 inhibition, and clobetasol is a potent topical corticosteroid, but their functions in OPCs were unknown.

To test whether miconazole or clobetasol enhance remyelination in vivo, we used a toxin-induced model whereby focal demyelinated lesions are generated in dorsal white matter of the spinal cord of adult mice by localized injection of lysolecithin (lysophosphatidylcholine (LPC)). In lesioned animals, demyelination is complete within 4 days, after which OPCs are recruited into the lesion. Widespread remyelination does not normally start until 14-21 days post lesion (d.p.l.), which provides a defined window from days 4 to 14 to test the efficacy of drugs to enhance the extent and rate of remyelination. Both miconazole (10 or 40 mg per kg (body weight)) and clobetasol (2 mg per kg) treatment induced a marked improvement within the lesions of treated mice compared with vehicle-treated controls. At 8 d.p.l. both drugs induced a significant increase in the number of newly generated CC1$^+$ oligodendrocytes in the lesion core (FIG. 2A, B). This was coincident with extensive MBP staining in the lesions of miconazole- and clobetasol- but not vehicle-treated animals at both 8 and 12 d.p.l. (FIG. 2A). Electron micrographs and tissue sections stained with toluidine blue demonstrated that miconazole and clobetasol each induced a striking increase in the extent of remyelination (FIG. 2C, D and FIG. 8A, B). At 12 d.p.l., lesions of vehicle-treated mice consisted mostly of unmyelinated axons (6% myelinated) while those of clobetasol- and miconazole-treated mice contained >70% remyelinated axons throughout the extent of the lesion (FIG. 2D). Analysis of myelin thickness relative to axon diameter (g ratio) at 12 d.p.l. revealed that miconazole- and clobetasol-induced myelin was thinner than intact myelin, a defining characteristic of remyelination (FIG. 2D).

We also evaluated whether miconazole or clobetasol could promote precocious myelination during development, in the absence of injury or disease. We treated mice at postnatal day 2—a time point that precedes widespread CNS myelination—daily for 4 days with drug or vehicle. In miconazole- and clobetasol-treated mice, we found a significant increase in the number of CC1$^+$ oligodendrocytes in the lateral corpus callosum compared with vehicle-treated mice (FIG. 9A). Additionally, we found a significantly larger portion of the corpus callosum was populated by MBP$^+$ fibre tracts in miconazole- and clobetasol-treated mice (Extended Data FIG. 9B). This suggests that clobetasol and miconazole enhance myelination in the absence of damage or disease. Collectively, the LPC demyelination and developmental mouse models demonstrate that miconazole and clobetasol each function to induce the differentiation of endogenous OPCs in the CNS and promote enhanced myelination.

To determine whether the drugs were working at a particular stage of the OPC differentiation process, we seeded OPCs in differentiation conditions and treated them with either miconazole or clobetasol at different time points (0, 16, 24, or 48 h), and assayed MBP expression at 72 h. For both miconazole and clobetasol, the number of MBP$^+$ oligodendrocytes present at 72 h was dependent on drug treatment within the first 24 h of differentiation (FIG. 3A).

In agreement with these data, treatment of differentiating OPCs with either drug for different durations (24, 48, 56, and 72 h) induced a progressive, time-dependent increase in the number of MBP$^+$ oligodendrocytes (FIG. 3B). These data suggest that both drugs function directly on OPCs early in the differentiation process. Additionally, neither drug showed a significant impact on astrocyte formation from OPCs in vitro, suggesting they probably function as direct inducers of oligodendrocyte differentiation (FIG. 3C).

Muscarinic receptor antagonists such as benztropine and clemastine have recently been identified as remyelinating agents. Therefore we tested whether miconazole or clobetasol function through the muscarinic acetylcholine pathway using functional cellular reporter assays of all muscarinic receptor subtypes (M1-M5). Neither miconazole nor clobetasol inhibited any of the five muscarinic receptor subtypes (FIG. 3D). We then profiled whether clobetasol or miconazole biochemically inhibited the activity of 414 different kinase isoforms. Neither clobetasol nor miconazole inhibited any of the kinases tested, suggesting their activity is not based on direct inhibition of protein kinases.

Figure 10:
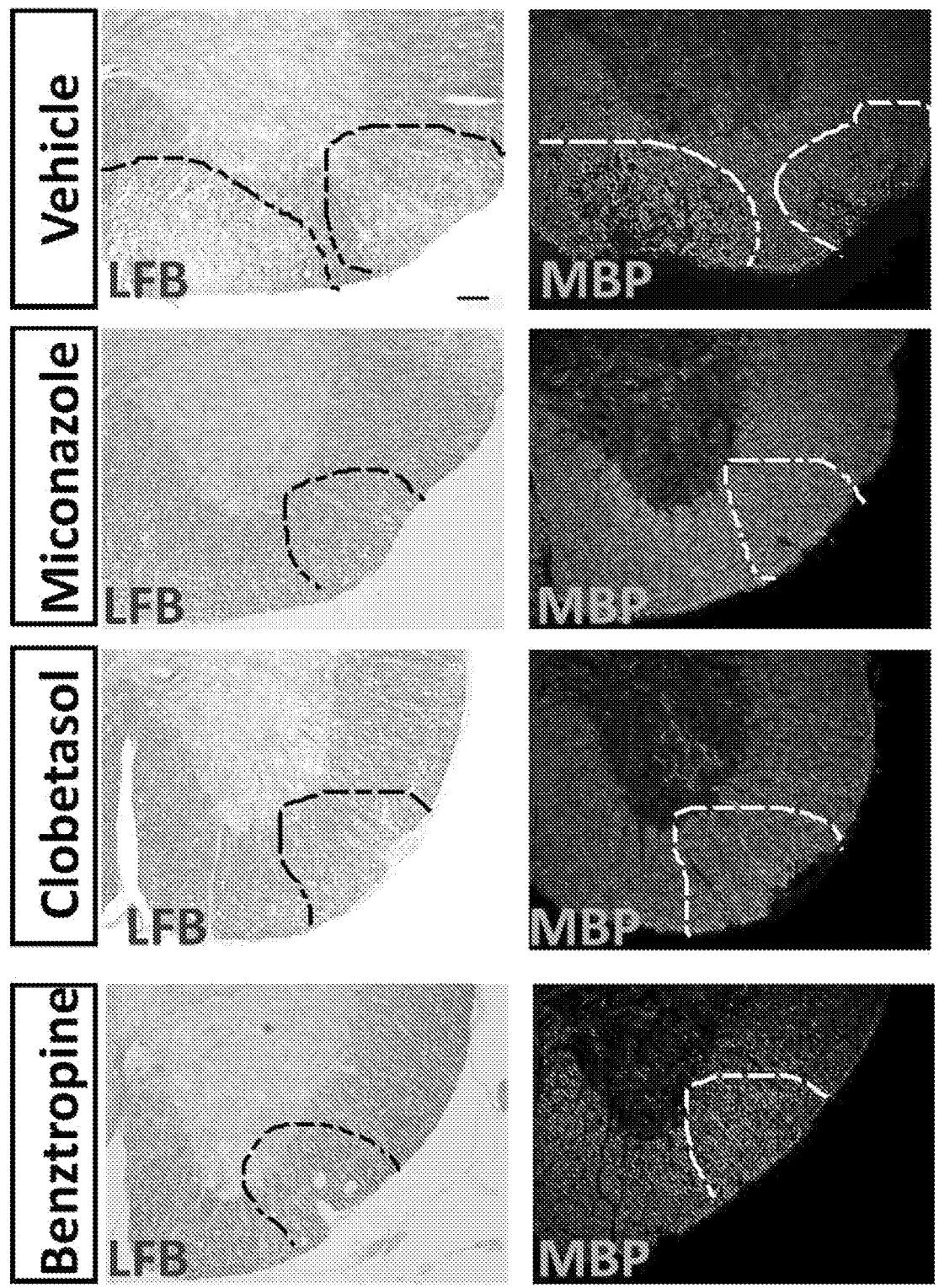
FIG. 10 illustrates spinal cords from MOG35-55 immunized EAE animals show regions of repair and remyelination. Cervical spinal cords from miconazole, clobetasol and benztropine treated animals show a decrease in areas of myelin disruption in the white matter as assayed by luxol fast blue and MBP immunohistochemistry. Lesions in the spinal cord are marked by dotted lines. Scale bar 100 µm.

To explore the signalling pathways in OPCs influenced by these drugs, we performed genome-wideRNA sequencing and phosphoproteomic analyses on mouse OPCs treated with drug or vehicle (FIG. 10A-C). Miconazole or clobetasol treatment altered OPC transcript expression and phosphoproteins within hours, and influenced expression of genes in signaling pathways involved in oligodendrocyte maturation and myelination. Clobetasol potently modulated genes downstream of multiple nuclear hormone receptors, including glucocorticoid receptor, which are known to be important regulators of myelin gene expression. Since glucocorticoid receptor signalling is also known to enhance Schwann-cell-mediated myelination in the peripheral nervous system, we tested whether the activity of clobetasol on OPCs was mediated by glucocorticoid receptor signalling. Treatment of OPCs with clobetasol for 1 h increased the phosphorylation of glucocorticoid receptor at Ser220, an activating post-translational modification (FIG. 3E). RU486, a competitive glucocorticoid receptor antagonist, blocked clobetasol-induced glucocorticoid receptor phosphorylation and oligodendrocyte differentiation (FIG. 3E, F) suggesting that the activity of clobetasol in OPCs is mediated through the glucocorticoid receptor signalling axis.

For miconazole, pathway analyses showed that proteins in the mitogen-activated protein (MAP) kinase pathway were most strongly affected (FIG. 11A, B). Most Prominent was the strong and sustained phosphorylation of both extracellular signal-regulated kinases ERK1 and ERK2 (ERK1/2) at canonical activation sites, which we validated by western blotting (FIG. 3G). In mice, genetic loss of ERK1/2 in the oligodendrocyte lineage results in normal numbers of OPCs and oligodendrocytes but widespread hypomyelination, while constitutive activation of ERK1/2 results in a profound increase in the extent of remyelination after toxin-induced demyelinating injury. In contrast tomiconazole, treatment of OPCs with clobetasol or benztropine did not induce ERK1/2 phosphorylation (FIG. 3G). Miconazole treatment of a non-neural cell type, mouse fibroblasts, also showed no increase of ERK1/2 phosphorylation, indicating potential cell-type specificity (FIG. 3G). PD0325901, a small molecule inhibitor of ERK's upstream MAP-kinase kinase (MEK), blocked the ability of miconazole to induce ERK1/2 phosphorylation, suggesting that miconazole functions through a MEK-dependent mechanism in OPCs (FIG. 3H). We also treated mouse OPCs with voriconazole, a triazole-containing antifungal cytochrome P450 inhibitor with 80% structural similarity to miconazole, which failed to induce changes in ERK1/2 phosphorylation (FIG. 3G). This was consistent with the observation that voriconazole did not promote the differentiation of OPCs into oligodendrocytes (FIG. 11C). Taken together, these results suggest that the effect of miconazole on OPCs is independent of cytochrome P450 inhibition.

We then assessed whether clobetasol and miconazole treatment would enhance the differentiation of human OPCs into oligodendrocytes. We generated human OPCs from humanembryonic stem cells (hESCs) and human-induced pluripotent stem cells (hiPSCs) (Extended Data FIG. 8A-C). We then treated human OPCs with DMSO, clobetasol, or miconazole for 21 days followed by staining for MBP, imaging, and HCA (FIG. 12D-G). Both drugs enhanced human OPC differentiation, with miconazole exhibiting the most reproducible and potent effects.

To interpret the potential impact of clobetasol or miconazole as therapeutics in immune-mediated MS models, we tested effects on immune cell survival and function. We found that only clobetasol, as expected from its known corticosteroid properties, altered naïve T-cell differentiation and both the proliferation and secretion of cytokines by proteolipid protein (PLP$_{139-151}$)- or myelin oligodendrocyte glycoprotein (MOG$_{35-55}$)-sensitized lymph node cells (FIG. 13A-J). As such, only clobetasol, but not the solely remyelinating drugs miconazole or benztropine, showed efficacy in reducing disease severity in the immune-driven relapsing-remitting PLP$_{139-151}$ experimental autoimmune encephalomyelitis (EAE) model (FIG. 4A). The positive effect of clobetasol in this model resulted from its immunosuppressive effects as evidenced by the severe reduction of T cells within the spleen (FIG. 4B).

We also used a second EAE mouse model, MOG$_{35-55}$-induced, in which the immune response was relatively controlled and disease pathology recapitulated chronic progressive demyelination. We used a therapeutic, rather than prophylactic, treatment regimen to evaluate whether drugs could reverse, rather than prevent, disease. Miconazole and clobetasol-treated animals all exhibited a marked improvement in function, with nearly all animals regaining use of one or both hind limbs (FIG. 4C, D). In contrast, vehicle-treated mice exhibited chronic hindlimb paralysis over the treatment period. Benztropine treatment also resulted in functional improvement, but to a lesser extent than miconazole and clobetasol (FIG. 4C, D). Overt functional recovery of miconazole- and clobetasol-treated mice correlated with histological improvements in the spinal cord. Specifically, drug-treated mice showed restoration of MBP expression and a reduction in the extent of demyelination in the spinal cord, whereas vehicle-treated mice showed sustained areas of white matter disruption (FIG. 14A-E).

Although the immunosuppressive effect of clobetasol makes it challenging to evaluate its remyelinating potential in EAE directly, its consistent and robust induction of OPC differentiation in vitro, and enhancement of remyelination in non-immune-driven in vivo assays, suggests that it serves a role in both immunomodulation and promotion of myelination. In contrast, miconazole did not modulate immune cell function and our data indicate that it acts as a direct remyelinating agent. Given the potential of miconazole as a remyelinating therapeutic, we contracted a separate laboratory to provide independent validation of its efficacy in the MOG$_{35-55}$-induced EAE preclinical model. The laboratory independently validated the preclinical efficacy of miconazole in MOG$_{35-55}$-induced EAE to reduce disease severity in treated mice (FIG. 4D).

Since the approval in 1993 of interferon (IFN)-β-1b for the treatment of MS, therapeutic development has centered on the generation of additional immunomodulatory agents. Despite the effectiveness of many of these drugs to modulate CNS inflammation in patients with MS, none of them prevent chronic progressive disease and disability—largely because of their inability to stop or reverse the failure of remyelination in the CNS. We developed an advanced high throughput screening platform to discover effective remyelinating therapeutics. This pluripotent stem-cell-based system provides unprecedented scalability, purity, and genotypic flexibility to screen for compounds that enhance OPC differentiation and myelination. Using this platform we identified two drugs approved by the US Food and Drug Administration, miconazole and clobetasol, with newly discovered functions to modulate OPC differentiation directly, enhance remyelination, and significantly reduce disease severity in mouse models of MS. Miconazole and clobetasol are currently only approved for topical administration in humans. However, the ability of miconazole and clobetasol to cross the blood-brain barrier raises the exciting possibility that these drugs, or modified derivatives, could advance into clinical trials for the currently untreatable chronic progressive phase of MS.

Methods

No statistical methods were used to predetermine sample size.

Mouse OPC Preparation

OPCs used in this study were generated from two separate EpiSC lines, EpiSC9 (female) and 129O1 (male), using in vitro differentiation protocols and culture conditions described previously. Cultures were regularly tested and shown to be mycoplasma free. To ensure uniformity throughout all in vitro screening experiments, EpiSC-derived OPCs were sorted to purity by fluorescent activated cell sorting at passage five with conjugated CD140a-APC (eBioscience, 17-1401; 1:80) and NG2-AF488 (Millipore, AB5320A4; 1:100) antibodies. Sorted batches of OPCs were expanded and frozen down in aliquots. OPCs were thawed into growth conditions for one passage before use in screening assays.

In Vitro Phenotypic Screening of OPCs

EpiSC-derived OPCs were seeded onto poly-D-lysine 96-well Viewplate or CellCarrier plates (PerkinElmer) coated with laminin (Sigma, L2020; 10 µgml$^{-1}$) using electronic multichannel pipetors. For the primary screen, 30,000 cells were seeded per well in screening medium (DMEM/F12 supplemented with N2 (R&D Systems), B-27 (Life Technologies), neurotrophin 3 (R&D Systems; 10 ng ml$^{-1}$), cAMP (Sigma; 50 µM), IGF-1 (R&D Systems; 100 ng ml$^{-1}$), noggin (R&D Systems; 100 ngml$^{-1}$)) and allowed to attach for 2 h before addition of drug. NIH Clinical Collection I and II drugs were added to assay plates with 0.1 ml pin replicators (Molecular Devices, Genetix; X5051), resulting in a final primary screening concentration of 5 µM. Thyroid-hormone-positive controls and DMSO vehicle controls were included in each assay plate. Cells were incubated under standard conditions (37° C., 5% $CO_2$) for 3 days and fixed with 4% paraformaldehyde (PFA) in phosphate buffered saline (PBS). Fixed plates were permeabilized with 0.1% Triton X-100 and blocked with 10% donkey serum (v/v) in PBS for 2 h. Cells were labelled with MBP antibodies (Abcam, ab7349; 1:100) for 1 h at room temperature (~22° C.) followed by detection with Alexa Fluorconjugated secondary antibodies (1:500) for 45 min. Nuclei were visualized by DAPI staining (Sigma; 1 µgml$^-$). All plates for the primary screen were processed and analyzed simultaneously to eliminate variability. Donepezil was identified in the primary screen; however, the drug was not available at the time of dose-response testing and was excluded from further testing.

Dose-response testing of drug hits followed the same procedure with the following modifications to eliminate any artefacts in the primary screen: independently sourced drugs; a distinct batch of EpiSC-derived OPCs from a mouse of opposite sex; multi-dose testing; cytotoxicity analysis; an alternative marker of mature oligodendrocytes proteolipid protein 1 (PLP1, antibody clone AA3 provided by B. Trapp; 1:5,000); and an alternative high content assay endpoint parameter (percentage of oligodendrocytes differentiated instead of process intensity and length parameters). All drugs were tested in quadruplicate at seven different doses (ranging from 333 nM to 6.7 µM) and classified into tiers on the basis of their half-maximum effective concentration ($EC_{50}$) to induce OPC maturation, and their toxicity (concentration at which 50% of the cells were lost). Tier A drugs (n=3) consisted of nanomolar dose effectors with little to no detectable toxicity at doses tested. Tier B drugs (n=4) showed nanomolar effects but demonstrated toxicity at high doses. Tier C and D drugs required high doses to see an effect, demonstrated toxicity at low doses, or failed to show a dose-dependent response.

HCA of In Vitro Screen

For the 5 µM in vitro screen, stained plates were imaged on the Opera confocal imaging system (PerkinElmer) and a set of 24×10 fields were collected from each well, resulting in an average of 10,000 cells being scored per well. For the dose-response (6.7 µM, 5 µM, 3.3 µM, 1.7 µM, 666 nM, 500 nM, and 333 nM) in vitro assays, plates were imaged on the Operetta High Content Imaging and Analysis system (PerkinElmer) and a set of 14×20 fields captured from each well resulting in an average of 3,300 cells being scored per well. Analysis (PerkinElmer Acapella, Harmony, and Columbus software) began by identifying intact nuclei stained by DAPI; that is, those traced nuclei that were larger than 50 µm$^2$ in surface area and possessed intensity levels that were typical and less than the threshold brightness of pyknotic cells. Each traced nucleus region was then expanded by 50% and cross-referenced with the mature myelin protein (MBP or PLP1) stain to identify oligodendrocyte nuclei, and from this the percentage of oligodendrocytes was calculated. Processes emanating from oligodendrocyte nuclei were identified using the CSIRO2 analysis module within a custom Acapella script. Maximum mean process length (denoted 'process length') and mean process intensity (denoted 'process intensity') were generated on a per well basis. For the 5 µM in vitro screen, values were calculated and normalized to 100 for thyroid hormone (positive control)-treated wells and to 0 for DMSO(vehicle)-treated wells, on a per plate basis.

Phenotypic Validation Testing of OPCs

Briefly, OPCs were grown and expanded in laminin-coated flasks before harvesting for plating. Cells were dispensed in screening media (see above for details) using a Multidrop Combi dispenser (Thermo Fisher) into laminin/poly-L-ornithine-coated sterile, 1,536-well, black clear-bottom tissue culture plates (Brooks Automation), to a final density of 2,000 cells per well. Plates were sealed with gasketed stainless steel lids with holes for gas exchange (Wako USA). Following cell attachment, library compounds were transferred by pintool (Wako USA) using 10 nl slotted pins. Library compounds were serially diluted in DMSO, and were added to plates to yield final concentrations of 0 (DMSO only), 4, and 20 µM compound. After incubation for 72 h at 37° C., cells were fixed, washed, and stained similar to the 96-wellOPCassay protocol, although all aspiration steps were performed using a Biotek EL406 Microplate Washer Dispenser (Biotek) equipped with a 1,536-well aspiration manifold. Dispense steps were performed with both peristaltic pump cassettes (for gentle reagent additions) and syringe pump manifolds (for faster bulk dispenses). Cells were stained with DAPI (Sigma; 1 μgml$^-$) and MBP antibody (Abcam, ab7349; 1:100). Plates were then imaged using an InCell 2000 Analyzer High Content Imager (GE Healthcare Bio-Sciences). Well images were analysed using InCell Analyzer Workstation software, and the MBP signal was quantified with a process detection algorithm, using total process skeleton length to qualify activity.

Ex Vivo Cerebellar Slice Cultures

Whole cerebellum was collected from C57BL/6 mice at postnatal day 7 and embedded in agarose. Sagittal slices were cut on a microtome (Leica) at 300 μm. Slices were cultured in a DMEM-Basal Medium Eagle's base with 15% heat inactivated horse serum, modified N2, and PDGF-AA. After 1 day in culture, slices were treated daily for 5 days with test drugs or vehicle (DMSO). Drugs tested were clobetasol (5 μM), hydroxyzine (5 μM), clotrimazole (2 μM), miconazole (1 μM), ketoconazole (1 μM), vesamicol (5 μM), propafenone (2 μM), dicyclomine (5 μM), benztropine (2 μM), haloperidol (5 μM), and medroxyprogesterone (5 μM). The identity of the drugs was blinded to the experimenter. Slices were then lysed for western blot or fixed in 4% PFA and processed for HCA as detailed below.

Immunohistochemistry

Immunohistochemistry was performed as previously described. In short, tissue sections or whole slices were washed three times in PBS, blocked in PBS containing Triton X-100 (0.1%) and normal donkey serum (NDS, 2% for sections and 10% for cerebellar slices) and incubated with primary antibody overnight. For MBP immunohistochemistry, the primary antibody solution consisted of 2% NDS, 2% bovine serum albumin, and 0.1% saponin. For all other antibodies, the primary antibody solution consisted of 2% NDS and 0.1% Triton X-100. Primary antibodies used included rat anti-MBP (Abcam, ab7349; 1:100), mouse anti-APC CC1 clone (Millipore, MABC200; 1:500), and rabbit anti-IBA1 (Wako Chemicals, 019-19741; 1:1,000). The tissue was then washed in PBS and incubated in secondary antibodies for 2 h. Secondary detection was performed with Alexa Fluor-conjugated secondary antibodies (1:500) for 1 h. Luxol fast blue staining was performed as previously described.

High Content Screen of Cerebellar Slices

MBP-stained cerebellar slices were analysed by confocal image on an Operetta system using PhenoLOGIC machine-learning technology within Harmony software. The software was trained to identify elongated fibres more characteristic of axonal ensheathment and to exclude regions of small fibres or diffuse background fluorescence on the basis of texture features. MBP-positive surface area was collected and normalized to the total surface area for the group of slices treated with each drug. A minimum of six slices were treated per drug, which included an equal distribution of medial and lateral slices.

Western Blotting of Cerebellar Slices

Cerebellar slices (each biological replicate using 12 slices per condition; six each from two separate animals) were collected in PBS and centrifuged. The PBS was aspirated and the pellet resuspended in 100 mL lysis buffer (20 mMTris, 137 mM NaCl, 5.0 mM EDTA pH 8.0, 10% glycerol, 1% NP40, pH to 8.0 with HCl), incubated on ice for 20 min, centrifuged, and the supernatant collected. Protein concentration was determined by a Pierce BCA protein assay kit (Thermo Fisher). Equal amounts of protein were applied to NuPAGE 12% Bis-TRIS gels (Life Technologies), and electrophoretically transferred onto a PVDF membrane (Life Technologies). The membranes were incubated with rabbit anti-MBP (Millipore, AB980; 1:500) and consequently probed with horseradish peroxidase (HRP)-conjugated goat anti-rabbit (1:5,000) or incubated with HRP-conjugated mouse anti-β-actin (Sigma, A3854; 1:10,000) to ensure even loading of samples. Enhanced chemiluminescence was performed with a West Pico kit (Thermo Fisher) and relative optical density was measured using ImageJ (NIH).

Chemoinformatics

Structure-activity searches of azoles and steranes were performed with Canvas program (Schrodinger Software, release 2014-1: Canvas, version 1.9). Tanimoto similarity between voriconazole and miconazole was calculated by ROCS (OpenEye Scientific Software).

Pharmacokinetics

C57BL/6 adult female mice were dosed intraperitoneally with miconazole (10 mg/kg or 40 mg/kg) or clobetasol (10 mg/kg). After 1 or 6 h, 100 ml of plasma was collected then each animal was perfused with PBS. Brains were collected, weighed, and rinsed with PBS. Water (0.5 ml) was added to the brain samples, which were then homogenized. Plasma and brain samples were each diluted fivefold with blank rat plasma. Three hundred microlitres of internal standard solution was added to the samples, vortexed, and centrifuged. Five microlitres of each sample was injected into an API-4000Qtrap mass spectrometer and quantified (Climax Labs).

Focal Demyelination and Drug Treatment

Focal demyelination in the spinal cord was induced by the injection of 1% LPC solution. Ten- to 12-week-old C57BL/6 female mice were anaesthetized using isoflurane and a T10 laminectomy was performed. One microlitre of 1% LPC was infused into the dorsal column at a rate of 15 ml h$^{-1}$. The animals were euthanized either at day 8 or day 12 after the laminectomy (n=6-9 per group). Animals that were euthanized at day 8 received vehicle or drug daily by intraperitoneal injection between days 3 and 7. Animals used in the day 12 experiments received vehicle or drug daily by intraperitoneal injection between days 4 and 11. Drugs were dissolved in DMSO and then diluted with sterile saline for injection. Mice were deeply anaesthetized using ketamine/xylazine rodent cocktail and then euthanized by transcardial perfusion with 4% PFA for histological analysis or 4% PFA, 2% gluteraldehyde, and 0.1M sodium cacodylate for electron microscopy. PFA fixed tissue was equilibrated in 30% sucrose, embedded in OCT, and cryosectioned at 20 μm thickness and processed for CC1 and MBP immunohistochemistry. ImageJ was used to measure area of the lesion and CC1$^+$ cells within the lesion were scored manually. For CC1 scoring, sections were taken from the centre of each lesion to control for lesion variability.

Electron Microscopy

Samples were processed as previously described. In short, samples were osmicated, stained en bloc with uranyl acetate, and embedded in EMbed 812, an Epon-812 substitute (EMS). Sections (1 μm) were cut and stained with toluidine blue and visualized on a light microscope (Leica DM5500B). Additional thin sections were cut, carbon coated and imaged either on a JEOL JEM-1200-EX electron microscope or a T12 electron microscope (FEI).

Developmental Myelination

Mouse pups of strain CD1 were administered 2 mg/kg clobetasol, 10 mg/kg miconazole, or vehicle (DMSO in saline) by daily intraperitoneal injections from postnatal day 2-6. Some clobetasol treated animals exhibited sickness on the basis of this treatment, with low body weight, and some animals of the cohort died before end of treatment. On postnatal day 6 the pups were anaesthetized using ketamine and xylazine and euthanized by transcardial perfusion with 4% PFA. Tissue was fixed overnight in 4% PFA, equilibrated in 30% sucrose, and embedded in OCT. Sections (20 µm) were cut and processed for CC1 and MBP immunohistochemistry. ImageJ was then used to count and measure area of the corpus callosum as well as measure the extent of the corpus callosum length covered by MBP1 processes. Eight coronal sections containing corpus callosum rostral to the hippocampus from at least three animals per group were used for these analyses. To quantitate extent of MBP in the corpus callosum, a line was drawn through the centre of the corpus callosum from the lateral tip to the dorsal most extent of MBP expression in the corpus callosum. The length of this line was measured and then the dorsal-most point of the line was extended to the dorsal tip of the corpus callosum and measured to yield the length of the lateral callosum. The two numbers were divided to get the MBP/corpus callosum proportion. A two-tailed t-test was used to compare drug— with vehicle-treated groups.

Muscarinic Receptor Antagonism

Miconazole, clobetasol, and benztropine (all at 1 µM in DMSO) were sent to Select Screen (Life Technologies) with identities coded. GeneBLAzer or Tango assays were performed to determine level of acetylcholine muscarinic receptor M1, M3, M5 (GeneBLAzer), M2 and M5 (Tango) antagonism.

Kinase Profiling

LanthaScreen, Z9-LYTE, and Adapta kinase assays were performed by Select Screen (Life Technologies). LanthaScreen Eu kinase assays were performed in Greiner low-volume 384-well plates. Assay buffer consisted of 50 mM HEPES pH 7.5, 0.01% BRIJ-35, 10 mM MgCl$_2$, 1 mM EGTA. Each well consisted of this mixture: 4.0 µl of 4 µM test drug in assay buffer, 8 µl of 2× kinase/Eu antibody mixture, and 4 µl of 4×Alexa Fluor 647 tracer. Plates were incubated for 60 min at room temperature (~22° C.), then Alexa Fluor 647 emission (665 nm) and Europium emission (615 nm) read on a fluorescent plate reader. Data were analysed by generating the emission ratio (665 nm/615 nm) for each test point and normalizing 0% to control wells with no known inhibitor and 100% to control wells with highest concentration of known inhibitor.

Z'-LYTE assays were performed in Corning, low volume 384-well plates. Assay buffer consisted of 50 mM HEPES pH 7.5, 0.01% BRIJ-35, 10 mM MgCl$_2$, 1 mM EGTA. Each well consisted of this mixture: 2.5 µl 4× of 4 µM drug in assay buffer, 5 µl 2× peptide/kinase mixture, 2.5 µl 4×ATP solution. Plates were then incubated at room temperature (~22° C.) for 60 min. Then 5 µl of a development reagent that contained a protease that selectively digested the non-phosphorylated peptide was added and the plates incubated for 60 min. Coumarin emission (445 nm) and fluorescein emission (520 nm) were read on a fluorescent plate reader. Data were analysed by normalizing out background fluorescence then generating the emission ratio (445 nm/520 nm) for each test point. Data were further normalized to 0% in control wells with no ATP and 100% in control wells with synthetically phosphorylated peptide of the same sequence.

Adapta assays were performed in Corning, low volume 384-well plates. Assay buffer consisted of 30 mMHEPES. Each well consisted of this mixture: 2.5 µl 4× of 4 µM drug in assay buffer, 2.5 µl 4×ATP solution, 5 µl 2× substrate/ kinase mixture. Plates were then incubated at room temperature (~22° C.) for 60 min. Then 5 µl of a development reagent that contained europium-anti-ADP antibody and ADP tracer were added and the plate incubated for 60 min. Alexa Fluor 647 emission (665 nm) and europium emission (615 nm) were read on a fluorescent plate reader. Data were analysed by generating the emission ratio (665 nm/615 nm) for each test point and normalizing 0% to control wells with no ATP in the kinase reaction and 100% to control wells with ADP.

HCA of Astrocyte Induction

For the astrocyte experiments in FIG. 3C, the experimental setup was identical to the PLP1-based primary validation screen except plates were stained for GFAP (DAKO, Z0334; 1:5,000). BMP4 (R&D Systems; 50 ng ml$^{-1}$) and LIF (Millipore; 10$^3$ U ml$^{-1}$) were used as the positive control for astrocyte induction. Assay plates were imaged on the Operetta High Content Imaging and Analysis system and a set of 14×20 fields captured. Columbus Data Management and Analysis System software (PerkinElmer) was used to quantify the percentage of GFAP1 astrocytes in each well using a method similar to that developed for oligodendrocytes.

Global Phosphoproteomics

Quantitative global phosphorylation studies were performed on OPCs across two different time points (1 and 5 h after treatment) with miconazole, clobetasol, or DMSO treatment using a label-free ultra-high performance liquid chromatography tandem mass spectrometry (LC-MS/MS) workflow without fractionation. Briefly, for each sample 30 million cells were lysed with 2% SDS solution with protease and phosphatase inhibitor (Thermo Fisher), and detergent was removed on 200 µl of the cell lysate using the FASP cleaning procedure. Each sample was digested by a two-step Lys-C/trypsin proteolytic cleavage and subjected to phospho-enrichment using a commercially available TiO2 enrichment spin tips (Thermo Fisher). LC-MS/MS analysis used a UPLC system (NanoAcquity, Waters) that was interfaced to an Orbitrap ProVelos Elite MS system (Thermo Fisher). Fold-change calculations were determined from peptide intensities for each drug versus DMSO at each time point. Phosphopeptides with greater than twofold change were imported into Ingenuity Pathway Analysis to elucidate signalling pathways perturbed with drug treatment.

RNA Sequencing and Analysis

Cells were lysed directly in 1 ml TRIzol (Invitrogen) and stored at −80° C. Once all samples were collected, samples were thawed on ice and separated with chloroform using Phase Lock Gel tubes (5 PRIME). RNA was isolated using the miRNeasy PlusMini Kit (Qiagen) according to the manufacturer's protocol. One microgram of each sample was then poly-A selected, fragmented, and library prepared using the TruSeqRNA Sample Prep Kit (Illumina) according to the manufacturer's protocol. Samples were indexed using TruSeq adapters. One hundred base-pair paired-end reads were generated for each sample on an Illumina HiSeq 2500 instrument at the Case Western Reserve University Genomics Core facility. Between 5 million and 13 million reads were generated per sample for drug time course experiments. EpiSC RNaseq data were previously published (GEOaccession number GSE57403). EpiSCs, EpiSC OPCs, and in vivo OPCs were sequenced to depths of 51,271,458 reads, 61,072,460 reads, and 62,530,709 reads, respectively. For in vivo isolated OPCs, CD140a$^+$ cells were immunopanned from the CNS of mouse pups at postnatal day 7 as described previously. Cells were then cultured for 5 days in identical culture conditions to EpiSC-derived OPCs before analysis.

Reference genome files were retrieved from Illumina iGenomes. Reads were aligned to the mm9 genome using Tophat version 2.0.8 with default settings. Expression values of known RefSeq genes were calculated in units of fragments per kilobase per million reads (FPKM) using Cufflinks version 2.0.2. Expression values were tabled to eliminate background signal by converting all values below 0.25 to 0, and subsequently adding 0.25 to all values. FPKMs were quantile normalized to correct for inter-sample variation. To identify genes whose expression was perturbed by drug treatments, duplicate samples of OPCs were treated with drug or vehicle for 2, 6, or 12 h. RNA sequencing data were tested for differential expression by comparing treatments to vehicle at each time point using Cuffdiff version 2.0.2. The collective list of changed genes for each drug was evaluated with Ingenuity Pathway Analysis (application build 261899, content version 18030641).

Western Blotting of Mouse OPCs

EpiSC-derived OPCs were seeded into poly-L-ornithine/laminin coated six-well plates and allowed to attach for 2 h in DMEM/F12 without additional factors. Cells were treated with indicated inhibitors or DMSO for 1 h-SCH772984 (ChemieTek, 1 mM), SB590885 (Tocris, 10 nM), LY294002 (Tocris, 10 μM), and PD0325901 (Stemgent, 1 μM). Cells were then stimulated with drug or FGF2 (R&DSystems; 20 ng ml$^{-1}$) for 1 h and then lysed in 200 μL RIPA buffer (0.15 M NaCl, 0.05M Tris, pH=8.0, 1 mM EDTA, 1% Triton X-100, 0.1% SDS, 10% glycerol, HALT protease and phosphatase inhibitor (Thermo Fisher) added just before use) and incubated on ice for 20 min. Lysates were centrifuged at 4° C. and supernatant collected. Protein concentrations were determined by Pierce BCA protein assay kit (Thermo Fisher). Equal amounts of protein were resolved in a reduced manner on NuPAGE 4-12% Bis-Tris gels (Life Technologies) and transferred onto PVDF membranes (Life Technologies). Blots were blocked in either 5% BSA (phosphoprotein) or 5% milk (non phosphoprotein). Primary antibodies were all from the same vendor (Cell Signaling) and included phospho-Erk1/2 (4370S, clone D13.14.4E; 1:2,000), ERK1/2 (9107S, clone 3A7; 1:2,000), phospho-glucocorticoid receptor (4161S; 1:1,000), and glucocorticoid receptor (12041, clone D6H2L; 1:1,000) followed by incubation with HRP-conjugated secondary antibodies and chemiluminescent enhancement by West Pico substrate (Thermo Fisher).

Generation and Screening of Human OPCs

Human OPCs were generated from skin fibroblast-derived human iPSC line (CWRU43, Tesar laboratory) and hESC lines H7 (NIH Human Embryonic StemCell RegistryWA07; NIH approval number NIHhESC-10-0061) and H9 (NIH Human Embryonic Stem Cell Registry WA09; NIH approval number NIHhESC-10-0062) as previously described. iPSC- and hESC-derived OPCs were characterized by Sox10 (R&D Systems, AF2864; 1:100) staining, and then seeded in 96-well plates at 40,000 cells per well for drug testing. Cells were cultured with 1 μM miconazole, 5 μM clobetasol, or vehicle (DMSO) for 21 days, with fresh media changes with drug or vehicle every 2 days. Plates were fixed and stained with MBP (Abcam, ab7349; 1:100) then imaged on the Operetta system. We analysed results with slight modification to HCA Acapella scripts used for mouse oligodendrocytes.

Naive CD41 T-Cell Assays

Naive CD4+ T cells (CD4+L-selectin$^{hi}$ cells) were purified using AutoMacs Magnetic Bead cell separation technology (Miltenyi Biotech) from total lymph node cells isolated from unprimed mice with purity ranging from 98 to 99.9%. For in vitro activation, $5\times10^5$ naive CD4$^+$ T cells were activated in the presence of plate-bound anti CD3 (1 μgml$^{-1}$) plus Th1—(200 U ml$^{-1}$ interleukin-2 (IL-2), 40 U ml$^{-1}$ IL-12, 10 μgml$^{-1}$ anti-IL-4) or Th17—(10 μg ml$^{-1}$ TGF-β1, 50 ng ml$^{-1}$ IL-6, 1 μgml$^{-1}$ anti-IFN-γ, 1 μgml$^{-1}$ anti-IL-4, 1 μgml$^{-1}$ anti-IL-2) promoting conditions. On day 4, the cultured T cells were collected and the percentage of viable cytokine positive cells assessed by flow cytometry. The cells were stained with a LIVE/DEAD Fixable Violet Dead Cell Stain Kit, for 405 nm excitation (Life Technologies), anti CD4-APC/Cy7 (clone RM4-5), anti-IFN-γ-PerCP/Cy5.5 (clone XMG1.2), and anti-IL-17-APC (clone eBio17B7) (eBioscience). Viable cells ($5\times10^5$) were analysed per individual sample using a BD Canto II cytometer (BD Biosciences), and the data were analysed using FloJo version 9.5.2 software (Tree Star).

Ex Vivo Lymphocyte Recall Assays

Female SJL/J (Harlan Laboratories) or C57BL/6 mice were housed under SPF conditions. Six- to seven-week-old female mice were immunized subcutaneously with 100 μl of an emulsion containing 200 μg of *Mycobacterium tuberculosis* H37Ra (BD Biosciences) and 50 μg of PLP$_{139-151}$ (SJL/J) or MOG$_{35-55}$ (C57BL/6) distributed over three sites on the flank. For ex vivo culture draining, lymph nodes on day 8 were collected and cells were activated in the presence of anti-CD3 (1 μgml$^{-1}$) in the absence or presence of clobetasol, miconazole, or benztropine ($10^{-9}$-$10^{-5}$ M). To assess total cellular proliferation, cultures were pulsed with tritiated thymidine (1 μCi) at 24 h and cultures were harvested at 72 h. In replicate wells, culture supernatants were harvested at 72 h after culture, and the level of IFN γ and IL-17 were assessed via Luminex assay (Millipore).

PLP$_{139-151}$-Induced Relapsing Remitting EAE

Six- to seven-week-old female SJL/J mice were induced with PLP$_{139-151}$ as for ex vivo recall assays. Mice were allowed to progress to disease onset at day 13 before being randomized into treatment groups (n=10 mice per group). Mice were then monitored for paralysis and treated daily by intraperitoneal injection with vehicle (DMSO in sterile saline), benztropine (10 mg/kg), clobetasol (2 mg/kg), or miconazole (10 mg/kg) beginning on day 13 and ending on day 29. This period fully encompassed the acute phase of disease onset followed by remission and the primary disease relapse. Treatments were blinded to the experimenters performing the assays. Mice were followed for disease severity in a blinded fashion with disease scoring as follows: 0, no abnormality; 1, limp tail; 2, limp tail and hind limb weakness; 3, hind limb paralysis; 4, hind limb paralysis and forelimb weakness; and 5, moribund.

MOG$_{35-55}$ Chronic Progressive EAE Model

EAE was induced by immunizing 10-week-old C57BL/6 female mice with 100 ml injection of MOG$_{355}$/5 complete Freund's adjuvant emulsion (Hooke Laboratories). One hour after immunization, mice were given 100 ng of pertussis toxin by 100 μl intraperitoneal injection. A second dose of pertussis toxin was administered the next day. EAE onset was monitored daily and scored using a clinical scale where 0 represented no abnormality; 1, limp tail; 2, limp tail and hind limb weakness; 3, hind limb paralysis; 4, hind limb paralysis and forelimb weakness; and 5, moribund. Mice that appeared moribund or exhibited forelimb paralysis were immediately euthanized and not used for the study. Once mice reached peak of disease ~day 15; clinical score=3) they were randomized into treatment groups, and drug or vehicle (DMSO in saline) was administered intraperitoneally daily for 10 days (n=12-16 mice per group). Doses for each drug were miconazole (10 mg/kg), clobetasol (2 mg/kg), and benztropine (10 mg/kg). At these doses, no drugs showed any overt evidence of toxicity to any of the animals. Experimenters were blinded to the identity of the treatments and animals were scored daily. Cumulative disease scores for each animal were calculated during the treatment period, and a two-tailed t-test compared drug—with vehicle-treated groups. The extent of recovery for each animal was calculated as the difference between the peak disease score and the score at the end of each experiment, and a two-tailed t-test was used to compare each treatment with vehicle. External validation of MOG$_{35-55}$ EAE experiments (n=12 mice per group) was performed at Hooke Laboratories with experimenters blinded to the identity of the substances. FTY720 (fingolimod, 1 mg/kg), a known immunomodulatory drug, was used as a positive control during external validation of miconazole (10 mg/kg).

While this invention has been shown and described with references to various embodiments thereof, it will be understood by those skilled in the art that changes in form and details may be made therein without departing from the scope of the invention encompassed by the appended claims. All patents, publications and references cited in the foregoing specification are herein incorporated by reference in their entirety.

What is claimed is:

1. A method of treating a myelination-related disorder characterized by chronic progressive demyelination in a subject in need thereof, the method comprising administering to the subject a therapeutically effective amount of a primary 1,3-diazole compound having the formula:

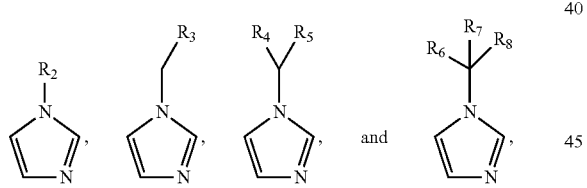

or a pharmaceutically acceptable salt thereof; wherein $R_2$, $R_3$, $R_4$, $R_5$, $R_6$, $R_7$, and $R_8$ are each individually one or more substituted or unsubstituted groups selected from:

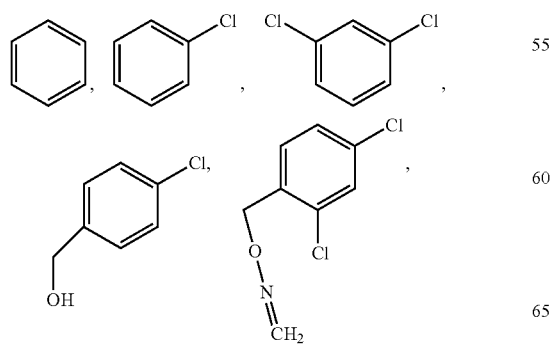

2. The method of claim 1, wherein the primary 1,3-diazole compound is represented by one of the following formulas:

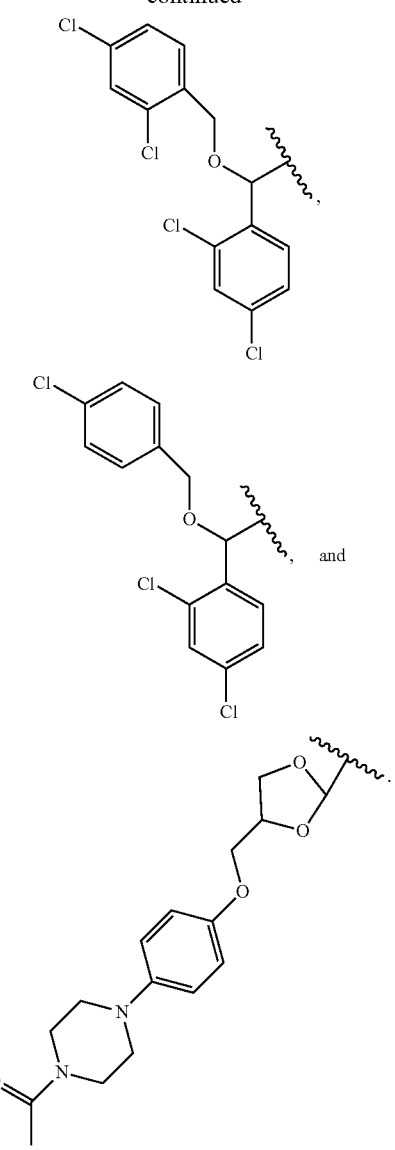

-continued

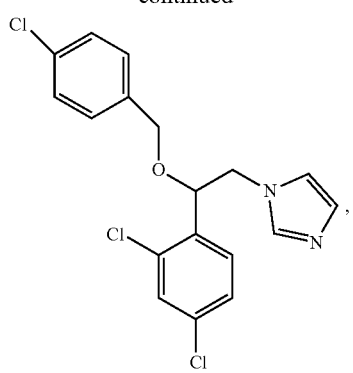

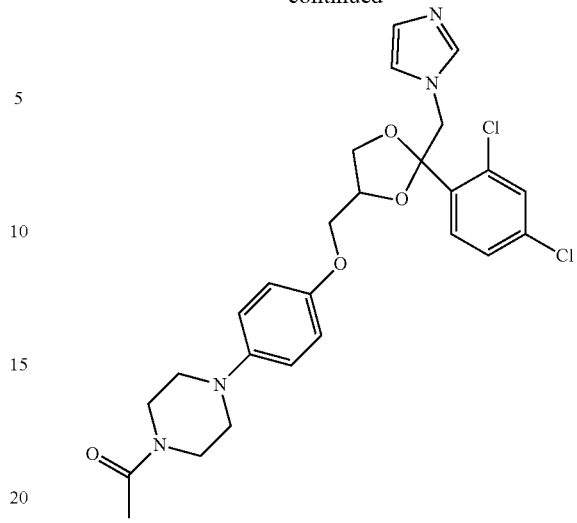

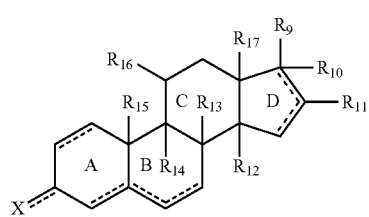

or an analog thereof.

3. The method of claim 1, wherein the myelination-related disorder is selected from multiple sclerosis, transverse myelitis, chronic inflammatory demyelinating polyneuropathy, and Guillain-Barre Syndrome.

4. The method of claim 1, wherein the myelination-related disorder is multiple sclerosis.

5. The method of claim 1, wherein the at least one (1,3) diazole compound is administered systemically.

6. The method of claim 1, further comprising administering to the subject a compound having the formula (II):

wherein:
(a) $R_9$, $R_{10}$, $R_{11}$, $R_{12}$, $R_{13}$, $R_{14}$, $R_{15}$, $R_{16}$, $R_{17}$ are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof, and wherein $R_{10}$ and $R_{11}$ may be linked to form a cyclic or polycyclic ring, wherein the ring is a substituted or unsubstituted aryl, heteroaryl, cycloalkyl, or heterocyclyl;

(b) the ABCD ring structure and/or one or more methyl group are independently optionally substituted with one or more substituents selected from $C_1$-$C_6$-alkyl, halogenated $C_1$-$C_6$-alkyl, $C_1$-$C_6$-alkenyl, halogenated $C_1$-$C_6$-alkenyl, halogen, amino, aminoalkylene, hydroxyimino, carbonyl (oxo), and hydroxy;

(c) X is OH or O; and (d) dashed lines are taken at each occurrence independently to be double or single bonds; and combinations thereof, or pharmaceutically acceptable salts thereof.

7. The method of claim 6, wherein $R_9$ is

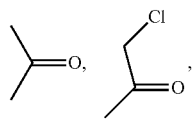

$CH_3$, $OCH_3$ or an alkyl halide.

8. The method of claim 6, wherein $R_{10}$ is H, hydroxyl or

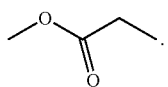

9. The method of claim 6, wherein the compound of formula (II) is represented by one of the following formulas:

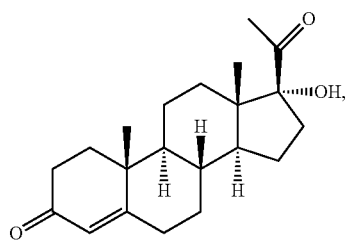

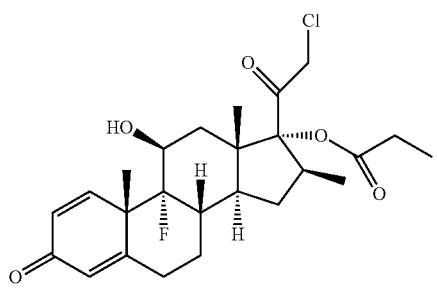

or an analog thereof.

* * * * *